US012799222B2

(12) United States Patent
Qu et al.

(10) Patent No.: US 12,799,222 B2
(45) Date of Patent: *Nov. 17, 2026

(54) ANTI-SIRPα ANTIBODY OR ANTIGEN-BINDING FRAGMENT THEREOF, AND USE THEREOF

(71) Applicant: QURE BIOTECHNOLOGY (SHANGHAI) CO., LTD., Shanghai (CN)

(72) Inventors: Xiangdong Qu, Shanghai (CN); Qin Pan, Shanghai (CN); Han Zheng, Shanghai (CN); Yejie Du, Shanghai (CN); Zishuo Chen, Shanghai (CN)

(73) Assignee: QURE BIOTECHNOLOGY (SHANGHAI) CO., LTD., Shanghai (CN)

( * ) Notice: Subject to any disclaimer, the term of this patent is extended or adjusted under 35 U.S.C. 154(b) by 671 days.

This patent is subject to a terminal disclaimer.

(21) Appl. No.: 18/254,941

(22) PCT Filed: Aug. 19, 2021

(86) PCT No.: PCT/CN2021/113416

§ 371 (c)(1),
(2) Date: May 30, 2023

(87) PCT Pub. No.: WO2022/110922

PCT Pub. Date: Jun. 2, 2022

(65) Prior Publication Data

US 2024/0018255 A1 Jan. 18, 2024

(30) Foreign Application Priority Data

Nov. 30, 2020 (CN) ......................... 202011372817.3
Dec. 29, 2020 (CN) ......................... 202011602742.3
Aug. 10, 2021 (CN) ......................... 202110911478.X

(51) Int. Cl.
*C07K 16/28* (2006.01)
*A61P 35/00* (2006.01)
*C12N 15/63* (2006.01)

(52) U.S. Cl.
CPC .......... *C07K 16/2896* (2013.01); *A61P 35/00* (2018.01); *C07K 16/2887* (2013.01);
(Continued)

(58) Field of Classification Search
None
See application file for complete search history.

(56) References Cited

FOREIGN PATENT DOCUMENTS

CN 110325549 A 10/2019
CN 110799536 A 2/2020
(Continued)

OTHER PUBLICATIONS

Weiskopf et al., Science. May 30, 2013;341(6141) (Year: 2013).*
(Continued)

*Primary Examiner* — Karl J Puttlitz
(74) *Attorney, Agent, or Firm* — NKL Law; Bin Lu; Allen Xue

(57) ABSTRACT

An anti-SIRPα antibody or an antigen-binding fragment thereof, and use thereof are provided. The anti-human SIRPα monoclonal antibody is obtained by means of immunizing mice, and a chimeric antibody and a humanized antibody are further obtained. The provided anti-SIRPα antibody or antigen-binding fragment thereof can bind to the human SIRPα protein, block the CD47-SIRPα signaling pathway, and have immune regulation effects such as enhancing phagocytosis. Further provided are a pharmaceutical composition and a nucleic acid molecule, and the use of the anti-SIRPα antibody or the antigen-binding fragment
(Continued)

thereof in the preparation of a drug for inhibiting or treating diseases.

19 Claims, 12 Drawing Sheets

Specification includes a Sequence Listing.

(52) U.S. Cl.
CPC .......... *C12N 15/63* (2013.01); *C07K 2317/52* (2013.01); *C07K 2317/565* (2013.01); *C07K 2317/567* (2013.01)

(56) References Cited

FOREIGN PATENT DOCUMENTS

| | | | | | |
|---|---|---|---|---|---|
| CN | 111448210 | A | | 7/2020 | |
| CN | 111635458 | A | | 9/2020 | |
| CN | 111995682 | A | | 11/2020 | |
| WO | 2018057669 | A1 | | 3/2018 | |
| WO | 2019226973 | A1 | | 11/2019 | |
| WO | WO-2023231705 | A1 | * | 12/2023 | ......... C07K 16/2827 |

OTHER PUBLICATIONS

Potential new cancer treatment activates cancer-engulfing cells, 2017, downloaded Mar. 4, 2016 from https://www.sciencedaily.com/releases/2017/02/170206084054.htm (Year: 2017).*

Yanagita et al., JCI Insight. Jan. 12, 2017;2(1):e89140 (Year: 2017).*

Ho, Chia Chi M. et al.; “Velcro”Engineering of High Affinity CD47 Ectodomain as Signal Regulatory Protein(SIRP alpha)Antagonists That Enhance Antibody-dependent Cellular Phagocytosis; Journal of Biological Chemistry, vol. 290, No. 20; May 15, 2015; pp. 12650-12663.

Voets, Erik et al.; “Functional characterization of the selective pan-allele anti-SIRPα antibody ADU-1805 that blocks the SIRPα -CD47 innate immune checkpoint”; Journal for Immuno Therapy of Cancer; vol. 7, No. 340; Published Dec. 4, 2019; pp. 1-15.

Uniprot P78324(31-149)( SIRPA-Tyrosine-protein phosphatase non-receptor type substrate 1 precursor—*Homo sapiens*(Human)—SIRPA gene&protein(uniprot.org); pp. 1-9.

Dondelinger, Mathieu et al.; “Understanding 1-15 the Significance and Implications of Antibody Numbering and Antigen-Binding Surface/Residue Definition”; Frontiers in Immunology, Oct. 16, 2018, vol. 9, Article 2278, pp. 1-15.

* cited by examiner

| | EC50 |
|---|---|
| QP2561589 | 0.001598 |
| QP256291 | 0.00157 |
| QP2561586 | 0.001199 |
| QP2561581 | 0.0009179 |
| QP2561594 | 0.001134 |
| QP256279 | 0.000819 |
| QP2561770 | 0.001302 |
| QP2561771 | 0.001062 |
| QP256253 | 0.001255 |
| QP163245 | 0.001626 |
| QP026249 | 0.02366 |

| | EC50 |
|---|---|
| QP2561589 | 0.002009 |
| QP256291 | 0.001178 |
| QP2561586 | 0.001236 |
| QP2561581 | 0.0007678 |
| QP2561594 | 0.0009833 |
| QP256279 | 0.0005584 |
| QP2561770 | 0.001035 |
| QP2561771 | 0.001138 |
| QP256253 | 0.00172 |
| QP163245 | 0.001186 |
| QP026249 | 0.001525 |

| | EC50 |
|---|---|
| Rituxmab | 0.01788 |
| Rituxmab+QP32260279 | 0.009829 |
| Rituxmab+QP32261586 | 0.008603 |
| Rituxmab+QP32261589 | 0.008546 |
| Rituxmab+QP32700279 | 0.006432 |
| Rituxmab+QP32701586 | 0.008719 |
| Rituxmab+QP32701589 | 0.008465 |
| Rituxmab+QP32260253 | 0.009252 |

| | EC50 |
|---|---|
| Rituxmab | 0.01788 |
| Rituxmab+QP32250279 | 0.008508 |
| Rituxmab+QP32550279 | 0.01213 |
| Rituxmab+QP32680279 | 0.01027 |
| Rituxmab+QP32650279 | 0.007549 |
| Rituxmab+QP32210026 | 0.01263 |
| Rituxmab+QP32680026 | 0.01169 |
| Rituxmab+QP32713240 | 0.01289 |
| Rituxmab+QP32260279 | 0.009829 |

| | EC50 |
|---|---|
| Rituximab | 0.02777 |
| Rituximab + QP32220163 | 0.01863 |
| Rituximab + QP32250253 | 0.0195 |
| Rituximab + QP32700279 | 0.01683 |
| Rituximab + QP32701586 | 0.01747 |
| Rituximab + QP32701589 | 0.01814 |
| Rituximab + QP32680026 | 0.01786 |
| Rituximab + QP32713240 | 0.02596 |

| | 18D5 | KWAR23 | CHO71 |
|---|---|---|---|
| EC50 | ~ 0.05542 | 0.1374 | 0.06819 |

| | 18D5 | KWAR23 | CHO71 |
|---|---|---|---|
| EC50 | ~ 58.68 | 0.1345 | 0.06351 |

| | 18D5 | KWAR23 | CHO71 |
|---|---|---|---|
| EC50 | 0.1248 | 0.1149 | 0.05738 |

| | 18D5 | KWAR23 | CHO71 |
|---|---|---|---|
| EC50 | 0.1304 | 0.1441 | 0.06911 |

| | 18D5 | KWAR23 | CHO71 |
|---|---|---|---|
| EC50 | 0.1138 | 0.1187 | 0.05299 |

| | 18D5 | KWAR23 | CHO71 |
|---|---|---|---|
| EC50 | ~ 110379876 | 0.1489 | 0.07069 |

| | 18D5 | KWAR23 | CHO71 |
|---|---|---|---|
| EC50 | ~ 0.02458 | 0.1803 | 0.08512 |

| | 18D5 | KWAR23 | CHO71 |
|---|---|---|---|
| EC50 | 0.1569 | 0.1808 | 0.08745 |

SEQUENCE LISTING

```
<160> NUMBER OF SEQ ID NOS: 61

<210> SEQ ID NO 1
<211> LENGTH: 133
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QP009(SIRPa)

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95
```

```
Gly Ser Pro Asp Asp Val Glu Phe Lys Ser Gly Ala Gly Thr Glu Leu
            100                 105                 110

Ser Val Arg Ala Lys Pro Ser Asp Tyr Lys Asp Asp Asp Asp Lys His
        115                 120                 125

His His His His His
    130


<210> SEQ ID NO 2
<211> LENGTH: 119
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 heavy chain variable region

<400> SEQUENCE: 2

Gln Val Gln Leu Gln Gln Pro Gly Thr Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Lys Ala Thr Leu Thr Val Asp Lys Ser Ser Asn Thr Ala Tyr
65                  70                  75                  80

Met Gln Leu Ser Ser Leu Thr Ser Gly Asp Ser Ala Val Tyr Tyr Cys
                85                  90                  95

Ala Met Asp Tyr Gly Ser Leu Tyr Ala Met Asp Tyr Trp Gly Arg Gly
            100                 105                 110

Thr Ser Val Thr Val Ser Ser
        115


<210> SEQ ID NO 3
<211> LENGTH: 5
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 VHCDR1

<400> SEQUENCE: 3

Asn Tyr Trp Ile Asn
1               5


<210> SEQ ID NO 4
<211> LENGTH: 17
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 VHCDR2

<400> SEQUENCE: 4

Met Ile Asp Pro Ser Asp Ser Glu Thr His Tyr Asn Gln Ile Phe Lys
1               5                   10                  15

Asp
```

<210> SEQ ID NO 5
<211> LENGTH: 10
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 VHCDR3

<400> SEQUENCE: 5

```
Asp Tyr Gly Ser Leu Tyr Ala Met Asp Tyr
1               5                   10
```

<210> SEQ ID NO 6
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 light chain variable region

<400> SEQUENCE: 6

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Asn Tyr Ile Phe Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Thr Phe Gly Gly Gly Thr Lys Leu Glu Ile Lys
            100                 105                 110
```

<210> SEQ ID NO 7
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 VLCDR1

<400> SEQUENCE: 7

```
Arg Ala Ser Lys Ser Val Ser Ser Ser Gly Tyr Asn Tyr Ile Phe
1               5                   10                  15
```

<210> SEQ ID NO 8
<211> LENGTH: 7
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 VLCDR2

<400> SEQUENCE: 8

```
Leu Ala Ser Asn Leu Asp Ser
1               5


<210> SEQ ID NO 9
<211> LENGTH: 8
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: 71C10 VLCDR3

<400> SEQUENCE: 9

Gln His Ser Arg Glu Leu Pro Thr
1               5


<210> SEQ ID NO 10
<211> LENGTH: 237
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD026 light chain

<400> SEQUENCE: 10

Met Asp Met Arg Val Pro Ala Gln Leu Leu Gly Leu Leu Leu Leu Trp
1               5                   10                  15

Phe Pro Gly Ser Arg Cys Gln Ile Val Leu Thr Gln Ser Pro Ala Ile
            20                  25                  30

Met Ser Ala Ser Pro Gly Glu Lys Val Thr Leu Thr Cys Ser Ala Ser
        35                  40                  45

Ser Ser Val Ser Ser Ser Tyr Leu Tyr Trp Tyr Gln Gln Lys Pro Gly
    50                  55                  60

Ser Ser Pro Lys Leu Trp Ile Tyr Ser Thr Ser Asn Leu Ala Ser Gly
65                  70                  75                  80

Val Pro Ala Arg Phe Ser Gly Ser Gly Ser Gly Thr Ser Tyr Ser Leu
                85                  90                  95

Thr Ile Ser Ser Met Glu Ala Glu Asp Ala Ala Ser Tyr Phe Cys His
            100                 105                 110

Gln Trp Ser Ser Tyr Pro Arg Thr Phe Gly Ala Gly Thr Lys Leu Glu
        115                 120                 125

Leu Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235
```

<210> SEQ ID NO 11
<211> LENGTH: 462
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD027 heavy chain

<400> SEQUENCE: 11

Met Glu Phe Gly Leu Ser Trp Leu Phe Leu Val Ala Ile Leu Lys Gly
1               5                   10                  15

Val Gln Cys Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Gln Gln Arg Thr Glu Gln Gly Leu
    50                  55                  60

Glu Trp Ile Gly Arg Ile Asp Pro Glu Asp Gly Glu Thr Lys Tyr Ala
65                  70                  75                  80

Pro Lys Phe Gln Asp Lys Ala Thr Ile Thr Ala Asp Thr Ser Ser Asn
                85                  90                  95

Thr Ala Tyr Leu His Leu Ser Ser Leu Thr Ser Glu Asp Thr Ala Val
            100                 105                 110

Tyr Tyr Cys Ala Arg Trp Gly Ala Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro

```
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 12
<211> LENGTH: 459
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD249 heavy chain

<400> SEQUENCE: 12

Met Glu Phe Gly Leu Ser Trp Leu Phe Leu Val Ala Ile Leu Lys Gly
1               5                   10                  15

Val Gln Cys Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Ile His Trp Val Gln Gln Arg Thr Glu Gln Gly Leu
    50                  55                  60

Glu Trp Ile Gly Arg Ile Asp Pro Glu Asp Gly Glu Thr Lys Tyr Ala
65                  70                  75                  80

Pro Lys Phe Gln Asp Lys Ala Thr Ile Thr Ala Asp Thr Ser Ser Asn
                85                  90                  95

Thr Ala Tyr Leu His Leu Ser Ser Leu Thr Ser Glu Asp Thr Ala Val
            100                 105                 110

Tyr Tyr Cys Ala Arg Trp Gly Ala Tyr Trp Gly Gln Gly Thr Leu Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
```

```
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
        355                 360                 365

Glu Met Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
        435                 440                 445

Thr Gln Lys Ser Leu Ser Leu Ser Leu Gly Lys
    450                 455


<210> SEQ ID NO 13
<211> LENGTH: 217
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD163 light chain

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ser Ser
            20                  25                  30

Gly Tyr Asn Tyr Ile Phe Trp Tyr Gln Gln Lys Pro Gly Gln Pro Pro
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Thr Phe Gly Gly Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
```

```
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 14
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD164 heavy chain

<400> SEQUENCE: 14

Gln Val Gln Leu Gln Gln Pro Gly Thr Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Lys Ala Thr Leu Thr Val Asp Lys Ser Ser Asn Thr Ala Tyr
65                  70                  75                  80

Met Gln Leu Ser Ser Leu Thr Ser Gly Asp Ser Ala Val Tyr Tyr Cys
                85                  90                  95

Ala Met Asp Tyr Gly Ser Leu Tyr Ala Met Asp Tyr Trp Gly Arg Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 15
<211> LENGTH: 465
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD245 heavy chain

<400> SEQUENCE: 15

Met Glu Phe Gly Leu Ser Trp Leu Phe Leu Val Ala Ile Leu Lys Gly
1               5                   10                  15

Val Gln Cys Gln Val Gln Leu Gln Gln Pro Gly Thr Glu Leu Val Arg
            20                  25                  30

Pro Gly Ala Ser Val Lys Leu Ser Cys Lys Ala Ser Gly Tyr Thr Phe
        35                  40                  45

Thr Asn Tyr Trp Ile Asn Trp Val Lys Gln Arg Pro Gly Gln Gly Leu
    50                  55                  60

Glu Trp Ile Ala Met Ile Asp Pro Ser Asp Ser Glu Thr His Tyr Asn
65                  70                  75                  80

Gln Ile Phe Lys Asp Lys Ala Thr Leu Thr Val Asp Lys Ser Ser Asn
                85                  90                  95

Thr Ala Tyr Met Gln Leu Ser Ser Leu Thr Ser Gly Asp Ser Ala Val
            100                 105                 110

Tyr Tyr Cys Ala Met Asp Tyr Gly Ser Leu Tyr Ala Met Asp Tyr Trp
        115                 120                 125

Gly Arg Gly Thr Ser Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160
```

```
Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465
```

<210> SEQ ID NO 16
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD253 light chain variable region

<400> SEQUENCE: 16

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Ser Ser
            20                  25                  30
```

```
Gly Tyr Asn Tyr Ile Phe Trp Tyr Gln Gln Lys Pro Gly Gln Pro Pro
        35                  40                  45

Lys Leu Leu Ile Tyr Leu Ala Ser Asn Leu Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Leu Pro Thr Phe Gly Gln Gly Thr Lys Leu Glu Ile Lys
            100                 105                 110


<210> SEQ ID NO 17
<211> LENGTH: 119
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD256 heavy chain variable region

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Met Asp Tyr Gly Ser Leu Tyr Ala Met Asp Tyr Trp Gly Arg Gly
            100                 105                 110

Thr Leu Val Thr Val Ser Ser
        115


<210> SEQ ID NO 18
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD279 light chain variable region

<400> SEQUENCE: 18

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Arg Ser Ser
            20                  25                  30

Gly Tyr Asn Trp Ile Phe Trp Tyr Gln Gln Lys Pro Gly Gln Pro Pro
        35                  40                  45

Lys Leu Leu Ile Tyr Leu Ala Ser Asn Arg Asp Ser Gly Val Pro Asp
    50                  55                  60

Arg Phe Ser Gly Ser Gly Ser Gly Thr Asp Phe Thr Leu Thr Ile Ser
```

65 70 75 80

Ser Leu Gln Ala Glu Asp Val Ala Val Tyr Tyr Cys Gln His Ser Arg
85 90 95

Glu Leu Pro Thr Phe Gly Gln Gly Thr Lys Leu Glu Ile Lys
100 105 110

<210> SEQ ID NO 19
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD291 light chain variable region

<400> SEQUENCE: 19

Asp Ile Val Leu Thr Gln Ser Pro Asp Ser Leu Ala Val Ser Leu Gly
1 5 10 15

Glu Arg Ala Thr Ile Asn Cys Arg Ala Ser Lys Ser Val Gly Ser Ser
20 25 30

Gly Tyr Asn Trp Leu Phe Trp Tyr Gln Gln Lys Pro Gly Gln Pro Pro
35 40 45

Lys Leu Leu Ile Tyr Leu Ala Ser Asn Arg Asp Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln His Ser Arg
85 90 95

Glu Leu Pro Thr Phe Gly Gln Gly Thr Lys Leu Glu Ile Lys
100 105 110

<210> SEQ ID NO 20
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1581 light chain variable region

<400> SEQUENCE: 20

Asp Ile Val Leu Thr Gln Ser Pro Asp Ser Leu Ala Val Ser Leu Gly
1 5 10 15

Glu Arg Ala Thr Ile Asn Cys Arg Ala Ser Lys Ser Val Ser Ser Ser
20 25 30

Gly Tyr Asn Tyr Ile Phe Trp Tyr Gln Gln Lys Pro Gly Gln Pro Pro
35 40 45

Lys Leu Leu Ile Tyr Leu Ala Ser Asn Leu Asp Pro Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln His Ser Arg
85 90 95

Glu Leu Pro Thr Phe Gly Gln Gly Thr Lys Leu Glu Ile Lys
100 105 110

<210> SEQ ID NO 21
<211> LENGTH: 110

<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1586 light chain variable region

<400> SEQUENCE: 21

Asp Ile Val Leu Thr Gln Ser Pro Asp Ser Leu Ala Val Ser Leu Gly
1 5 10 15

Glu Arg Ala Thr Ile Asn Cys Arg Ala Ser Lys Ser Val Ser Ser Ser
20 25 30

Gly Tyr Asn Tyr Ile Phe Trp Tyr Gln Gln Lys Pro Gly Gln Pro Pro
35 40 45

Lys Leu Leu Ile Tyr Leu Ala Ser Asn Leu Asp Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Glu Ser Arg
85 90 95

Glu Leu Pro Thr Phe Gly Gln Gly Thr Lys Leu Glu Ile Lys
100 105 110

<210> SEQ ID NO 22
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1589 light chain variable region

<400> SEQUENCE: 22

Asp Ile Val Leu Thr Gln Ser Pro Asp Ser Leu Ala Val Ser Leu Gly
1 5 10 15

Glu Arg Ala Thr Ile Asn Cys Arg Ala Ser Lys Ser Val Ser Ser Ser
20 25 30

Gly Tyr Asn Tyr Ile Phe Trp Tyr Gln Gln Lys Pro Gly Gln Pro Pro
35 40 45

Lys Leu Leu Ile Tyr Leu Ala Ser Asn Leu Asp Ser Gly Val Pro Asp
50 55 60

Arg Phe Ser Gly Ser Gly Ser Gly Thr Asp Phe Thr Leu Thr Ile Ser
65 70 75 80

Ser Leu Gln Ala Glu Asp Val Ala Val Tyr Tyr Cys Gln Glu Ser Trp
85 90 95

Glu Leu Pro Thr Phe Gly Gln Gly Thr Lys Leu Glu Ile Lys
100 105 110

<210> SEQ ID NO 23
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1594 light chain variable region

<400> SEQUENCE: 23

Asp Ile Val Leu Thr Gln Ser Pro Asp Ser Leu Ala Val Ser Leu Gly

```
1               5                   10                  15

Glu Arg Ala Thr Ile Asn Cys Arg Ala Ser Lys Ser Val Ser Ser Ser
            20                  25                  30

Gly Tyr Asn Tyr Ile Phe Trp Tyr Gln Gln Lys Pro Gly Gln Pro Pro
        35                  40                  45

Lys Leu Leu Ile Tyr Leu Ala Ser Asn Leu Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Asp Leu Pro Thr Phe Gly Gln Gly Thr Lys Leu Glu Ile Lys
            100                 105                 110


<210> SEQ ID NO 24
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1770 light chain variable region

<400> SEQUENCE: 24

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Arg Ser Ser
            20                  25                  30

Gly Tyr Asn Trp Ile Phe Trp Tyr Gln Gln Lys Pro Gly Gln Pro Pro
        35                  40                  45

Lys Leu Leu Ile Tyr Leu Ala Ser Asn Arg Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Glu Ser Arg
                85                  90                  95

Glu Leu Pro Thr Phe Gly Gln Gly Thr Lys Leu Glu Ile Lys
            100                 105                 110


<210> SEQ ID NO 25
<211> LENGTH: 110
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1771 light chain variable region

<400> SEQUENCE: 25

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Ser Val Ser Ser Ser
            20                  25                  30

Gly Tyr Asn Trp Ile Phe Trp Tyr Gln Gln Lys Pro Gly Gln Pro Pro
        35                  40                  45

Lys Leu Leu Ile Tyr Leu Ala Ser Asn Arg Asp Ser Gly Val Pro Asp
    50                  55                  60
```

```
Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Glu Ser Arg
                85                  90                  95

Glu Leu Pro Thr Phe Gly Gln Gly Thr Lys Leu Glu Ile Lys
            100                 105                 110


<210> SEQ ID NO 26
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3270 heavy chain

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Met Asp Tyr Gly Ser Leu Tyr Ala Met Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Ala Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

Lys

<210> SEQ ID NO 27
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3225 heavy chain

<400> SEQUENCE: 27

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Ile Asn Trp Val Arg Gln Ala Pro Gly Gln Gly Leu Glu Trp Ile
35 40 45

Ala Met Ile Asp Pro Ser Asp Ser Glu Thr His Tyr Asn Gln Ile Phe
50 55 60

Lys Asp Arg Ala Thr Leu Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Met Asp Tyr Gly Ser Leu Tyr Ala Met Asp Tyr Trp Gly Arg Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro

```
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gln Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 28
<211> LENGTH: 446
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3226 heavy chain

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Met Asp Tyr Gly Ser Leu Tyr Ala Met Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Gln Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445
```

```
<210> SEQ ID NO 29
<211> LENGTH: 445
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3255 heavy chain

<400> SEQUENCE: 29
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Met Asp Tyr Gly Ser Leu Tyr Ala Met Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415
```

```
Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 30
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3260 heavy chain

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Met Asp Tyr Gly Ser Leu Tyr Ala Met Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 31
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3265 heavy chain

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Ile
        35                  40                  45

Ala Met Ile Asp Pro Ser Asp Ser Glu Thr His Tyr Asn Gln Ile Phe
    50                  55                  60

Lys Asp Arg Ala Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Met Asp Tyr Gly Ser Leu Tyr Ala Met Asp Tyr Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 32
<211> LENGTH: 443
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3268 heavy chain

<400> SEQUENCE: 32

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
            85                  90                  95

Ala Arg Trp Gly Ala Tyr Trp Gly Gln Gly Thr Leu Val Thr Val Ser
            100                 105                 110
```

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Ala Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 33
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3271 heavy chain

<400> SEQUENCE: 33

Gln Val Gln Leu Gln Gln Ser Gly Pro Glu Leu Val Lys Pro Gly Ala
1               5                   10                  15

```
Ser Val Arg Ile Ser Cys Lys Ala Ser Gly Phe Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Phe Cys
                85                  90                  95

Ala Arg Pro Thr Ile Ile Ala Thr Asp Phe Asp Val Trp Gly Ala Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Ala Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
435 440 445

Lys

<210> SEQ ID NO 34
<211> LENGTH: 449
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3222 heavy chain

<400> SEQUENCE: 34

Gln Val Gln Leu Gln Gln Pro Gly Thr Glu Leu Val Arg Pro Gly Ala
1 5 10 15

Ser Val Lys Leu Ser Cys Lys Ala Ser Gly Tyr Thr Phe Thr Asn Tyr
20 25 30

Trp Ile Asn Trp Val Lys Gln Arg Pro Gly Gln Gly Leu Glu Trp Ile
35 40 45

Ala Met Ile Asp Pro Ser Asp Ser Glu Thr His Tyr Asn Gln Ile Phe
50 55 60

Lys Asp Lys Ala Thr Leu Thr Val Asp Lys Ser Ser Asn Thr Ala Tyr
65 70 75 80

Met Gln Leu Ser Ser Leu Thr Ser Gly Asp Ser Ala Val Tyr Tyr Cys
85 90 95

Ala Met Asp Tyr Gly Ser Leu Tyr Ala Met Asp Tyr Trp Gly Arg Gly
100 105 110

Thr Ser Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Gln Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys

```
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 35
<211> LENGTH: 440
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3221 heavy chain

<400> SEQUENCE: 35

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220
```

```
Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Gln Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 36
<211> LENGTH: 236
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD3240 light chain

<400> SEQUENCE: 36

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser His Lys Phe
            20                  25                  30

Met Ser Thr Ser Val Gly Asp Arg Val Asn Ile Thr Cys Lys Ala Ser
        35                  40                  45

Gln Gly Val Gly Thr Ala Val Gly Trp Tyr Gln Gln Lys Pro Gly Gln
    50                  55                  60

Ser Pro Arg Leu Leu Ile Tyr Trp Ala Ser Thr Arg His Thr Gly Val
65                  70                  75                  80

Pro Asp Arg Phe Thr Gly Ser Gly Ser Gly Thr Asp Phe Ser Leu Ala
                85                  90                  95

Ile Ser Asn Val Gln Ser Glu Asp Leu Ala Asp Tyr Phe Cys Gln Gln
            100                 105                 110

Tyr Ser Thr Tyr Pro Phe Thr Phe Gly Gly Gly Thr Asn Leu Glu Ile
        115                 120                 125
```

```
Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 37
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD279/QD1770 VLCDR1

<400> SEQUENCE: 37

Arg Ala Ser Gln Ser Val Arg Ser Ser Gly Tyr Asn Trp Ile Phe
1               5                   10                  15


<210> SEQ ID NO 38
<211> LENGTH: 7
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD279/QD291/QD1770/QD1771 VLCDR2

<400> SEQUENCE: 38

Leu Ala Ser Asn Arg Asp Ser
1               5


<210> SEQ ID NO 39
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD291 VLCDR1

<400> SEQUENCE: 39

Arg Ala Ser Lys Ser Val Gly Ser Ser Gly Tyr Asn Trp Leu Phe
1               5                   10                  15


<210> SEQ ID NO 40
<211> LENGTH: 7
<212> TYPE: PRT
<213> ORGANISM: Artificial Sequence
<220> FEATURE:
<223> OTHER INFORMATION: synthesized
<220> FEATURE:
<221> NAME/KEY: misc_feature
```

<223> OTHER INFORMATION: QD1581 VLCDR2

<400> SEQUENCE: 40

Leu Ala Ser Asn Leu Asp Pro
1 5

<210> SEQ ID NO 41
<211> LENGTH: 8
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1586/QD1770/QD1771 VLCDR3

<400> SEQUENCE: 41

Gln Glu Ser Arg Glu Leu Pro Thr
1 5

<210> SEQ ID NO 42
<211> LENGTH: 8
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1589 VLCDR3

<400> SEQUENCE: 42

Gln Glu Ser Trp Glu Leu Pro Thr
1 5

<210> SEQ ID NO 43
<211> LENGTH: 8
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1594 VLCDR3

<400> SEQUENCE: 43

Gln His Ser Arg Asp Leu Pro Thr
1 5

<210> SEQ ID NO 44
<211> LENGTH: 15
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QD1771 VLCDR1

<400> SEQUENCE: 44

Arg Ala Ser Lys Ser Val Ser Ser Ser Gly Tyr Asn Trp Ile Phe
1 5 10 15

<210> SEQ ID NO 45
<211> LENGTH: 376
<212> TYPE: PRT
<213> ORGANISM: Artificial Sequence
<220> FEATURE:
<223> OTHER INFORMATION: synthesized
<220> FEATURE:

```
<221> NAME/KEY: misc_feature
<223> OTHER INFORMATION: QP094

<400> SEQUENCE: 45

Met Glu Phe Gly Leu Ser Trp Leu Phe Leu Val Ala Ile Leu Lys Gly
1               5                   10                  15

Val Gln Cys Glu Glu Glu Leu Gln Val Ile Gln Pro Asp Lys Ser Val
            20                  25                  30

Leu Val Ala Ala Gly Glu Thr Ala Thr Leu Arg Cys Thr Ala Thr Ser
        35                  40                  45

Leu Ile Pro Val Gly Pro Ile Gln Trp Phe Arg Gly Ala Gly Pro Gly
    50                  55                  60

Arg Glu Leu Ile Tyr Asn Gln Lys Glu Gly His Phe Pro Arg Val Thr
65                  70                  75                  80

Thr Val Ser Asp Leu Thr Lys Arg Asn Asn Met Asp Phe Ser Ile Arg
                85                  90                  95

Ile Gly Asn Ile Thr Pro Ala Asp Ala Gly Thr Tyr Tyr Cys Val Lys
            100                 105                 110

Phe Arg Lys Gly Ser Pro Asp Asp Val Glu Phe Lys Ser Gly Ala Gly
        115                 120                 125

Thr Glu Leu Ser Val Arg Ala Lys Pro Ser Ala Pro Val Val Ser Gly
    130                 135                 140

Pro Ala Ala Arg Ala Thr Pro Gln His Thr Val Ser Phe Thr Cys Glu
145                 150                 155                 160

Ser His Gly Phe Ser Pro Arg Asp Ile Thr Leu Lys Trp Phe Lys Asn
                165                 170                 175

Gly Asn Glu Leu Ser Asp Phe Gln Thr Asn Val Asp Pro Val Gly Glu
            180                 185                 190

Ser Val Ser Tyr Ser Ile His Ser Thr Ala Lys Val Val Leu Thr Arg
        195                 200                 205

Glu Asp Val His Ser Gln Val Ile Cys Glu Val Ala His Val Thr Leu
    210                 215                 220

Gln Gly Asp Pro Leu Arg Gly Thr Ala Asn Leu Ser Glu Thr Ile Arg
225                 230                 235                 240

Val Pro Pro Thr Leu Glu Val Thr Gln Gln Pro Val Arg Ala Glu Asn
                245                 250                 255

Gln Val Asn Val Thr Cys Gln Val Arg Lys Phe Tyr Pro Gln Arg Leu
            260                 265                 270

Gln Leu Thr Trp Leu Glu Asn Gly Asn Val Ser Arg Thr Glu Thr Ala
        275                 280                 285

Ser Thr Val Thr Glu Asn Lys Asp Gly Thr Tyr Asn Trp Met Ser Trp
    290                 295                 300

Leu Leu Val Asn Val Ser Ala His Arg Asp Asp Val Lys Leu Thr Cys
305                 310                 315                 320

Gln Val Glu His Asp Gly Gln Pro Ala Val Ser Lys Ser His Asp Leu
                325                 330                 335

Lys Val Ser Ala His Pro Lys Glu Gln Gly Ser Asn Thr Ala Ala Glu
            340                 345                 350

Asn Thr Gly Ser Asn Glu Arg Gly Ser Ser Asp Tyr Lys Asp Asp Asp
        355                 360                 365

Asp Lys His His His His His His
    370                 375

<210> SEQ ID NO 46
```

<211> LENGTH: 375
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QP096

<400> SEQUENCE: 46

```
Met Glu Phe Gly Leu Ser Trp Leu Phe Leu Val Ala Ile Leu Lys Gly
1               5                   10                  15

Val Gln Cys Glu Glu Glu Leu Gln Val Ile Gln Pro Asp Lys Ser Val
            20                  25                  30

Ser Val Ala Ala Gly Glu Ser Ala Ile Leu His Cys Thr Val Thr Ser
        35                  40                  45

Leu Ile Pro Val Gly Pro Ile Gln Trp Phe Arg Gly Ala Gly Pro Ala
    50                  55                  60

Arg Glu Leu Ile Tyr Asn Gln Lys Glu Gly His Phe Pro Arg Val Thr
65                  70                  75                  80

Thr Val Ser Glu Ser Thr Lys Arg Glu Asn Met Asp Phe Ser Ile Ser
                85                  90                  95

Ile Ser Asn Ile Thr Pro Ala Asp Ala Gly Thr Tyr Tyr Cys Val Lys
            100                 105                 110

Phe Arg Lys Gly Ser Pro Asp Thr Glu Phe Lys Ser Gly Ala Gly Thr
        115                 120                 125

Glu Leu Ser Val Arg Ala Lys Pro Ser Ala Pro Val Val Ser Gly Pro
    130                 135                 140

Ala Ala Arg Ala Thr Pro Gln His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Val Gly Glu Ser
            180                 185                 190

Val Ser Tyr Ser Ile His Ser Thr Ala Lys Val Val Leu Thr Arg Glu
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Glu Thr Ile Arg Val
225                 230                 235                 240

Pro Pro Thr Leu Glu Val Thr Gln Gln Pro Val Arg Ala Glu Asn Gln
                245                 250                 255

Val Asn Val Thr Cys Gln Val Arg Lys Phe Tyr Pro Gln Arg Leu Gln
            260                 265                 270

Leu Thr Trp Leu Glu Asn Gly Asn Val Ser Arg Thr Glu Thr Ala Ser
        275                 280                 285

Thr Val Thr Glu Asn Lys Asp Gly Thr Tyr Asn Trp Met Ser Trp Leu
    290                 295                 300

Leu Val Asn Val Ser Ala His Arg Asp Asp Val Lys Leu Thr Cys Gln
305                 310                 315                 320

Val Glu His Asp Gly Gln Pro Ala Val Ser Lys Ser His Asp Leu Lys
                325                 330                 335

Val Ser Ala His Pro Lys Glu Gln Gly Ser Asn Thr Ala Ala Glu Asn
            340                 345                 350

Thr Gly Ser Asn Glu Arg Gly Ser Ser Asp Tyr Lys Asp Asp Asp Asp
        355                 360                 365
```

```
Lys His His His His His His
    370                 375


<210> SEQ ID NO 47
<211> LENGTH: 375
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QP098

<400> SEQUENCE: 47

Met Glu Phe Gly Leu Ser Trp Leu Phe Leu Val Ala Ile Leu Lys Gly
1               5                   10                  15

Val Gln Cys Glu Glu Glu Leu Gln Val Ile Gln Pro Glu Lys Ser Val
            20                  25                  30

Ser Val Ala Ala Gly Asp Ser Ala Thr Leu Asn Cys Thr Val Ser Ser
        35                  40                  45

Leu Ile Pro Val Gly Pro Ile Gln Trp Phe Arg Gly Ala Gly Pro Gly
    50                  55                  60

Arg Glu Leu Ile Tyr Asn Leu Lys Glu Gly His Phe Pro Arg Val Thr
65                  70                  75                  80

Ala Val Ser Asp Pro Thr Lys Arg Asn Asn Met Asp Phe Ser Ile Arg
                85                  90                  95

Ile Ser Asn Ile Thr Pro Ala Asp Ala Gly Thr Tyr Tyr Cys Val Lys
            100                 105                 110

Phe Arg Lys Gly Ser Pro Asp Val Glu Leu Lys Ser Gly Ala Gly Thr
        115                 120                 125

Glu Leu Ser Val Arg Ala Lys Pro Ser Ala Pro Val Val Ser Gly Pro
    130                 135                 140

Ala Val Arg Ala Thr Ala Glu His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Val Gln Thr Asn Val Asp Pro Ala Gly Lys Ser
            180                 185                 190

Val Ser Tyr Ser Ile Arg Ser Thr Ala Arg Val Leu Leu Thr Arg Arg
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Glu Ala Ile Arg Val
225                 230                 235                 240

Pro Pro Phe Leu Glu Val Thr Gln Gln Ser Met Arg Ala Asp Asn Gln
                245                 250                 255

Val Asn Val Thr Cys Gln Val Thr Lys Phe Tyr Pro Gln Arg Leu Gln
            260                 265                 270

Leu Thr Trp Leu Glu Asn Gly Asn Val Ser Arg Thr Glu Met Ala Ser
        275                 280                 285

Ala Leu Pro Glu Asn Lys Asp Gly Thr Tyr Asn Trp Thr Ser Trp Leu
    290                 295                 300

Leu Val Asn Val Ser Ala His Arg Asp Asp Val Lys Leu Thr Cys Gln
305                 310                 315                 320

Val Glu His Asp Gly Gln Pro Ala Val Asn Lys Ser Phe Ser Val Lys
                325                 330                 335
```

```
Val Ser Ala His Pro Lys Glu Gln Gly Ser Asn Thr Ala Ala Glu Asn
            340                 345                 350

Thr Gly Thr Asn Glu Arg Gly Ser Ser Asp Tyr Lys Asp Asp Asp Asp
        355                 360                 365

Lys His His His His His His
    370                 375
```

<210> SEQ ID NO 48
<211> LENGTH: 375
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QP100

<400> SEQUENCE: 48

```
Met Glu Phe Gly Leu Ser Trp Leu Phe Leu Val Ala Ile Leu Lys Gly
1               5                   10                  15

Val Gln Cys Glu Glu Glu Leu Gln Val Ile Gln Pro Glu Lys Ser Val
            20                  25                  30

Ser Val Ala Ala Gly Glu Ser Ala Thr Leu Asn Cys Thr Ala Thr Ser
        35                  40                  45

Leu Ile Pro Val Gly Pro Ile Gln Trp Phe Arg Gly Val Gly Pro Gly
    50                  55                  60

Arg Glu Leu Ile Tyr His Gln Lys Glu Gly His Phe Pro Arg Val Thr
65                  70                  75                  80

Pro Val Ser Asp Pro Thr Lys Arg Asn Asn Met Asp Phe Ser Ile Arg
                85                  90                  95

Ile Ser Asn Ile Thr Pro Ala Asp Ala Gly Thr Tyr Tyr Cys Val Lys
            100                 105                 110

Phe Arg Lys Gly Ser Pro Asp Val Glu Leu Lys Ser Gly Ala Gly Thr
        115                 120                 125

Glu Leu Ser Val Arg Ala Lys Pro Ser Ala Pro Val Val Ser Gly Pro
    130                 135                 140

Ala Val Arg Ala Thr Ala Glu His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Ala Gly Lys Ser
            180                 185                 190

Val Ser Tyr Ser Ile Arg Ser Thr Ala Arg Val Val Leu Thr Arg Arg
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Glu Ala Ile Arg Val
225                 230                 235                 240

Pro Pro Phe Leu Glu Phe Thr Gln Gln Ser Met Arg Ala Asp Asn Gln
                245                 250                 255

Val Asn Val Thr Cys Gln Val Met Lys Phe Tyr Pro Gln Arg Leu Gln
            260                 265                 270

Leu Thr Trp Leu Glu Asn Gly Asn Val Ser Arg Thr Glu Met Ala Ser
        275                 280                 285

Ala Leu Pro Glu Asn Lys Asp Gly Thr Tyr Asn Trp Thr Ser Trp Leu
    290                 295                 300
```

```
Leu Val Asn Val Ser Ala His Arg Asp Asp Val Lys Leu Thr Cys Gln
305                 310                 315                 320

Val Glu His Asp Gly Gln Pro Ala Val Asn Lys Ser Phe Ser Val Lys
                325                 330                 335

Val Ser Ala His Pro Lys Glu Gln Gly Ser Asn Thr Ala Ala Glu Asn
            340                 345                 350

Thr Gly Thr Asn Glu Arg Gly Ser Ser Asp Tyr Lys Asp Asp Asp Asp
        355                 360                 365

Lys His His His His His His
    370                 375


<210> SEQ ID NO 49
<211> LENGTH: 372
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QP271

<400> SEQUENCE: 49

Met Glu Phe Gly Leu Ser Trp Leu Phe Leu Val Ala Ile Leu Lys Gly
1               5                   10                  15

Val Gln Cys Glu Glu Glu Leu Gln Val Ile Gln Pro Glu Lys Ser Val
            20                  25                  30

Ser Val Ala Ala Gly Asp Ser Ala Thr Leu Asn Cys Thr Val Thr Ser
        35                  40                  45

Leu Ile Pro Val Gly Pro Ile Gln Trp Phe Arg Gly Ala Gly Pro Gly
    50                  55                  60

Arg Glu Leu Ile Tyr His Gln Lys Glu Gly His Phe Pro Arg Val Thr
65                  70                  75                  80

Ser Val Ser Glu Ser Thr Lys Arg Asn Asn Met Asp Phe Ser Ile His
                85                  90                  95

Ile Ser Asn Ile Thr Pro Ala Asp Ala Gly Thr Tyr Tyr Cys Val Lys
            100                 105                 110

Phe Arg Lys Gly Ser Pro Asp Val Glu Val Lys Ser Gly Ala Gly Thr
        115                 120                 125

Glu Leu Ser Val Arg Ala Lys Pro Ser Ala Pro Val Val Ser Gly Pro
    130                 135                 140

Ala Val Arg Ala Thr Ala Glu His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Ala Gly Lys Ser
            180                 185                 190

Val Ser Tyr Ser Ile Arg Ser Thr Ala Arg Val Val Leu Thr Arg Arg
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Glu Ala Ile Arg Val
225                 230                 235                 240

Pro Pro Phe Leu Glu Val Thr Gln Gln Ser Met Arg Ala Asp Asn Gln
                245                 250                 255

Val Asn Val Thr Cys Gln Val Thr Lys Phe Tyr Pro Gln Arg Leu Gln
            260                 265                 270
```

```
Leu Thr Trp Leu Glu Asn Gly Asn Val Ser Arg Thr Glu Met Ala Ser
        275                 280                 285

Ala Leu Pro Glu Asn Lys Asp Gly Thr Tyr Asn Trp Thr Ser Trp Leu
    290                 295                 300

Leu Val Asn Val Ser Ala His Arg Asp Asp Val Lys Leu Thr Cys Gln
305                 310                 315                 320

Val Glu His Asp Gly Gln Pro Ala Val Asn Lys Ser Phe Ser Val Lys
                325                 330                 335

Val Ser Ala His Pro Lys Glu Gln Gly Ser Asn Thr Ala Ala Glu Asn
            340                 345                 350

Thr Gly Thr Asn Glu Arg Asp Tyr Lys Asp Asp Asp Asp Lys His His
        355                 360                 365

His His His His
    370
```

<210> SEQ ID NO 50
<211> LENGTH: 372
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: QP273

<400> SEQUENCE: 50

```
Met Glu Phe Gly Leu Ser Trp Leu Phe Leu Val Ala Ile Leu Lys Gly
1               5                   10                  15

Val Gln Cys Glu Glu Glu Leu Gln Val Ile Gln Pro Glu Lys Ser Val
            20                  25                  30

Ser Val Ala Ala Gly Glu Ser Ala Thr Leu Asn Cys Thr Ala Thr Ser
        35                  40                  45

Leu Ile Pro Val Gly Pro Ile Gln Trp Phe Arg Gly Val Gly Pro Gly
    50                  55                  60

Arg Glu Leu Ile Tyr Ser Gln Lys Glu Gly His Phe Pro Arg Val Thr
65                  70                  75                  80

Pro Val Ser Asp Pro Thr Lys Arg Asn Asn Met Asp Phe Ser Ile Arg
                85                  90                  95

Ile Ser Asn Ile Thr Pro Ala Asp Ala Gly Thr Tyr Tyr Cys Val Lys
            100                 105                 110

Phe Arg Lys Gly Ser Pro Asp Val Glu Leu Lys Ser Gly Ala Gly Thr
        115                 120                 125

Glu Leu Ser Val Arg Ala Lys Pro Ser Ala Pro Val Val Ser Gly Pro
    130                 135                 140

Ala Val Arg Ala Thr Ala Glu His Thr Val Ser Phe Thr Cys Glu Ser
145                 150                 155                 160

His Gly Phe Ser Pro Arg Asp Ile Thr Leu Lys Trp Phe Lys Asn Gly
                165                 170                 175

Asn Glu Leu Ser Asp Phe Gln Thr Asn Val Asp Pro Ala Gly Lys Ser
            180                 185                 190

Val Ser Tyr Ser Ile Arg Ser Thr Ala Arg Val Val Leu Thr Arg Arg
        195                 200                 205

Asp Val His Ser Gln Val Ile Cys Glu Val Ala His Val Thr Leu Gln
    210                 215                 220

Gly Asp Pro Leu Arg Gly Thr Ala Asn Leu Ser Glu Ala Ile Arg Val
225                 230                 235                 240
```

Pro Pro Phe Leu Glu Val Thr Gln Gln Ser Met Arg Ala Asp Asn Gln
245 250 255

Val Asn Val Thr Cys Gln Val Thr Lys Phe Tyr Pro Gln Arg Leu Gln
260 265 270

Leu Thr Trp Leu Glu Asn Gly Asn Val Ser Arg Thr Glu Met Ala Ser
275 280 285

Ala Leu Pro Glu Asn Lys Asp Gly Thr Tyr Asn Trp Thr Ser Trp Leu
290 295 300

Leu Val Asn Val Ser Ala His Arg Asp Asp Val Lys Leu Thr Cys Gln
305 310 315 320

Val Glu His Asp Gly Gln Pro Ala Val Asn Lys Ser Phe Ser Val Lys
325 330 335

Val Ser Ala His Pro Lys Glu Gln Gly Ser Asn Thr Ala Ala Glu Asn
340 345 350

Thr Gly Thr Asn Glu Arg Asp Tyr Lys Asp Asp Asp Asp Lys His His
355 360 365

His His His His
370

<210> SEQ ID NO 51
<211> LENGTH: 123
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V1

<400> SEQUENCE: 51

Gly Val Ala Gly Glu Glu Glu Leu Gln Val Ile Gln Pro Asp Lys Ser
1 5 10 15

Val Leu Val Ala Ala Gly Glu Thr Ala Thr Leu Arg Cys Thr Ala Thr
20 25 30

Ser Leu Ile Pro Val Gly Pro Ile Gln Trp Phe Arg Gly Ala Gly Pro
35 40 45

Gly Arg Glu Leu Ile Tyr Asn Gln Lys Glu Gly His Phe Pro Arg Val
50 55 60

Thr Thr Val Ser Asp Leu Thr Lys Arg Asn Asn Met Asp Phe Ser Ile
65 70 75 80

Arg Ile Gly Asn Ile Thr Pro Ala Asp Ala Gly Thr Tyr Tyr Cys Val
85 90 95

Lys Phe Arg Lys Gly Ser Pro Asp Asp Val Glu Phe Lys Ser Gly Ala
100 105 110

Gly Thr Glu Leu Ser Val Arg Ala Lys Pro Ser
115 120

<210> SEQ ID NO 52
<211> LENGTH: 122
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V2

<400> SEQUENCE: 52

Gly Val Ala Gly Glu Glu Glu Leu Gln Val Ile Gln Pro Asp Lys Ser

```
1               5                   10                  15

Val Ser Val Ala Ala Gly Glu Ser Ala Ile Leu His Cys Thr Val Thr
            20                  25                  30

Ser Leu Ile Pro Val Gly Pro Ile Gln Trp Phe Arg Gly Ala Gly Pro
        35                  40                  45

Ala Arg Glu Leu Ile Tyr Asn Gln Lys Glu Gly His Phe Pro Arg Val
    50                  55                  60

Thr Thr Val Ser Glu Ser Thr Lys Arg Glu Asn Met Asp Phe Ser Ile
65                  70                  75                  80

Ser Ile Ser Asn Ile Thr Pro Ala Asp Ala Gly Thr Tyr Tyr Cys Val
                85                  90                  95

Lys Phe Arg Lys Gly Ser Pro Asp Thr Glu Phe Lys Ser Gly Ala Gly
            100                 105                 110

Thr Glu Leu Ser Val Arg Ala Lys Pro Ser
        115                 120


<210> SEQ ID NO 53
<211> LENGTH: 122
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V3

<400> SEQUENCE: 53

Gly Val Ala Gly Glu Glu Glu Leu Gln Val Ile Gln Pro Asp Lys Ser
1               5                   10                  15

Val Ser Val Ala Ala Gly Glu Ser Ala Ile Leu Leu Cys Thr Val Thr
            20                  25                  30

Ser Leu Ile Pro Val Gly Pro Ile Gln Trp Phe Arg Gly Ala Gly Pro
        35                  40                  45

Ala Arg Glu Leu Ile Tyr Asn Gln Lys Glu Gly His Phe Pro Arg Val
    50                  55                  60

Thr Thr Val Ser Glu Ser Thr Lys Arg Glu Asn Met Asp Phe Ser Ile
65                  70                  75                  80

Ser Ile Ser Asn Ile Thr Pro Ala Asp Ala Gly Thr Tyr Tyr Cys Val
                85                  90                  95

Lys Phe Arg Lys Gly Ser Pro Asp Thr Glu Phe Lys Ser Gly Ala Gly
            100                 105                 110

Thr Glu Leu Ser Val Arg Ala Lys Pro Ser
        115                 120


<210> SEQ ID NO 54
<211> LENGTH: 123
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V4

<400> SEQUENCE: 54

Gly Val Ala Gly Glu Glu Gly Leu Gln Val Ile Gln Pro Asp Lys Ser
1               5                   10                  15

Val Ser Val Ala Ala Gly Glu Ser Ala Ile Leu His Cys Thr Ala Thr
            20                  25                  30
```

```
Ser Leu Ile Pro Val Gly Pro Ile Gln Trp Phe Arg Gly Ala Gly Pro
        35                  40                  45

Gly Arg Glu Leu Ile Tyr Asn Gln Lys Glu Gly His Phe Pro Arg Val
    50                  55                  60

Thr Thr Val Ser Asp Leu Thr Lys Arg Asn Asn Met Asp Phe Ser Ile
65                  70                  75                  80

Arg Ile Gly Asn Ile Thr Pro Ala Asp Ala Gly Thr Tyr Tyr Cys Val
                85                  90                  95

Lys Phe Arg Lys Gly Ser Pro Asp Asp Val Glu Phe Lys Ser Gly Ala
            100                 105                 110

Gly Thr Glu Leu Ser Val Arg Ala Lys Pro Ser
        115                 120


<210> SEQ ID NO 55
<211> LENGTH: 123
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V5

<400> SEQUENCE: 55

Gly Val Ala Gly Glu Glu Glu Leu Gln Val Ile Gln Pro Asp Lys Phe
1               5                   10                  15

Val Leu Val Ala Ala Gly Glu Thr Ala Thr Leu Arg Cys Thr Ala Thr
            20                  25                  30

Ser Leu Ile Pro Val Gly Pro Ile Gln Trp Phe Arg Gly Ala Gly Pro
        35                  40                  45

Gly Arg Glu Leu Ile Tyr Asn Gln Lys Glu Gly His Phe Pro Arg Val
    50                  55                  60

Thr Thr Val Ser Asp Leu Thr Lys Arg Asn Asn Met Asp Phe Ser Ile
65                  70                  75                  80

Arg Ile Gly Asn Ile Thr Pro Ala Asp Ala Gly Thr Tyr Tyr Cys Val
                85                  90                  95

Lys Phe Arg Lys Gly Ser Pro Asp Asp Val Glu Phe Lys Ser Gly Ala
            100                 105                 110

Gly Thr Glu Leu Ser Val Arg Ala Lys Pro Ser
        115                 120


<210> SEQ ID NO 56
<211> LENGTH: 123
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V6

<400> SEQUENCE: 56

Gly Val Ala Gly Glu Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
            20                  25                  30

Ser Leu Ile Pro Val Gly Pro Ile Gln Trp Phe Arg Gly Ala Gly Pro
        35                  40                  45

Gly Arg Glu Leu Ile Tyr Asn Gln Lys Glu Gly His Phe Pro Arg Val
    50                  55                  60
```

```
Thr Thr Val Ser Asp Leu Thr Lys Arg Asn Asn Met Asp Phe Pro Ile
65                  70                  75                  80

Arg Ile Gly Asn Ile Thr Pro Ala Asp Ala Gly Thr Tyr Tyr Cys Val
                85                  90                  95

Lys Phe Arg Lys Gly Ser Pro Asp Asp Val Glu Phe Lys Ser Gly Ala
            100                 105                 110

Gly Thr Glu Leu Ser Val Arg Ala Lys Pro Ser
        115                 120


<210> SEQ ID NO 57
<211> LENGTH: 122
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V7

<400> SEQUENCE: 57

Gly Val Ala Gly Glu Glu Glu Leu Gln Val Ile Gln Pro Asp Lys Ser
1               5                   10                  15

Val Ser Val Ala Ala Gly Glu Ser Ala Ile Leu His Cys Thr Val Thr
            20                  25                  30

Ser Leu Ile Pro Val Gly Pro Ile Gln Trp Phe Arg Gly Ala Gly Pro
        35                  40                  45

Ala Arg Glu Leu Ile Tyr Asn Gln Lys Glu Gly His Phe Pro Arg Val
    50                  55                  60

Thr Thr Val Ser Glu Ser Thr Lys Arg Glu Asn Met Asp Phe Ser Ile
65                  70                  75                  80

Ser Ile Ser Asn Ile Thr Pro Ala Asp Ala Gly Thr Tyr Tyr Cys Val
                85                  90                  95

Lys Phe Arg Lys Gly Ser Pro Asp Thr Glu Phe Lys Ser Gly Ala Gly
            100                 105                 110

Thr Glu Leu Ser Val Arg Gly Lys Pro Ser
        115                 120


<210> SEQ ID NO 58
<211> LENGTH: 122
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V8

<400> SEQUENCE: 58

Gly Val Ala Gly Glu Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
            20                  25                  30

Ser Leu Ile Pro Val Gly Pro Ile Gln Trp Phe Arg Gly Ala Gly Pro
        35                  40                  45

Ala Arg Glu Leu Ile Tyr Asn Gln Lys Glu Gly His Phe Pro Arg Val
    50                  55                  60

Thr Thr Val Ser Glu Ser Thr Lys Arg Glu Asn Met Asp Phe Ser Ile
65                  70                  75                  80

Ser Ile Ser Asn Ile Thr Pro Ala Asp Ala Gly Thr Tyr Tyr Cys Val
```

```
                85                  90                  95

Lys Phe Arg Lys Gly Ser Pro Asp Thr Glu Phe Lys Ser Gly Ala Gly
            100                 105                 110

Thr Glu Leu Ser Val Arg Ala Lys Pro Ser
        115                 120


<210> SEQ ID NO 59
<211> LENGTH: 123
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V9

<400> SEQUENCE: 59

Gly Val Ala Gly Glu Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
            20                  25                  30

Ser Leu Ile Pro Val Gly Pro Ile Gln Trp Phe Arg Gly Ala Gly Pro
        35                  40                  45

Gly Arg Glu Leu Ile Tyr Asn Gln Lys Glu Gly His Phe Pro Arg Val
    50                  55                  60

Thr Thr Val Ser Asp Leu Thr Lys Arg Asn Asn Met Asp Phe Ser Ile
65                  70                  75                  80

Arg Ile Ser Asn Ile Thr Pro Ala Asp Ala Gly Thr Tyr Tyr Cys Val
                85                  90                  95

Lys Phe Arg Lys Gly Ser Pro Asp Asp Val Glu Phe Lys Ser Gly Ala
            100                 105                 110

Gly Thr Glu Leu Ser Val Arg Ala Lys Pro Ser
        115                 120


<210> SEQ ID NO 60
<211> LENGTH: 122
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: SIRPa V10

<400> SEQUENCE: 60

Arg Val Ala Gly Glu Glu Glu Leu Gln Val Ile Gln Pro Asp Lys Ser
1               5                   10                  15

Val Ser Val Ala Ala Gly Glu Ser Ala Ile Leu His Cys Thr Val Thr
            20                  25                  30

Ser Leu Ile Pro Val Gly Pro Ile Gln Trp Phe Arg Gly Ala Gly Pro
        35                  40                  45

Ala Arg Glu Leu Ile Tyr Asn Gln Lys Glu Gly His Phe Pro Arg Val
    50                  55                  60

Thr Thr Val Ser Glu Ser Thr Lys Arg Glu Asn Met Asp Phe Ser Ile
65                  70                  75                  80

Ser Ile Ser Asn Ile Thr Pro Ala Asp Ala Gly Thr Tyr Tyr Cys Val
                85                  90                  95

Lys Phe Arg Lys Gly Ser Pro Asp Thr Glu Phe Lys Ser Gly Ala Gly
            100                 105                 110
```

-continued

```
Thr Glu Leu Ser Val Arg Ala Lys Pro Ser
        115                 120


<210> SEQ ID NO 61
<211> LENGTH: 233
<212> TYPE: PRT
<213> ORGANISM: Artificial Sequence
<220> FEATURE:
<223> OTHER INFORMATION: synthesized
<220> FEATURE:
<221> NAME/KEY: misc_feature
<223> OTHER INFORMATION: FC(mouse IgG2a)

<400> SEQUENCE: 61

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

ANTI-SIRPα ANTIBODY OR ANTIGEN-BINDING FRAGMENT THEREOF, AND USE THEREOF

INCORPORATION OF SEQUENCE LISTING

This application contains a sequence listing submitted in Computer Readable Form (CRF). The CFR file contains the sequence listing entitled "PBA408-0120 ST25 amended.txt", which was created on May 28, 2023, and is 118,743 bytes in size. The information in the sequence listing is incorporated herein by reference in its entirety.

TECHNICAL FIELD

The present invention relates to the technical field of biomedicine, in particular to an anti-SIRPα antibody or antigen-binding fragment thereof, and use thereof.

BACKGROUND

According to AACR estimates, in 2018, the number of newly diagnosed cases of malignant tumors in the United States will reach 1.8 million, and the number of deaths due to cancer will exceed 600 thousand, second only to heart disease. According to data released by the National Cancer Center of China, a total of 3.8 million cases of cancer cases were newly diagnosed in China in 2014, and the number of deaths due to cancer reached 2.3 million that year. Uncontrolled cell proliferation is a key factor in the formation of malignant tumors. In order to accelerate their own growth and protect themselves from being attacked by the body's immune system, tumor cells have obtained a series of ways to escape the immune monitoring of host in the long process of evolution. According to the cancer immunoediting theory proposed by Schreiber, the relationship between tumor cells and the host immune system can be divided into three different stages: elimination, equilibrium and escape. In the "elimination" state, the neonatal tumor cells have strong antigenicity and are easy to be recognized and eliminated by the immune system, while the tumor cells that survive through the elimination will enter the "equilibrium" state with the immune system, showing a state of host tumor-bearing survival. However, when their gene mutations under the selective pressure of the host immune system accumulate to a certain extent, tumor cells will break the equilibrium and enter the final "escape" state. Tumor cells at this stage can represent a series of malignant phenotypes, turn off the tumor suppressor response mechanism, induce normal immune response, and thus be recognized as normal cells. The apoptosis signaling pathway in tumor cells is also changed, which makes the mechanism of tumor cell apoptosis induced by immune cells ineffective. In addition, due to the rapid growth of tumor cells without inhibition, the formed tissue structure will produce a microenvironment that suppresses immune cells. In the tumor microenvironment, tumor cells release immunosuppressive molecules, such as VEGF, TGF-β, IL-10, etc., which inhibit the activation and differentiation of myeloid dendritic cells, thereby inhibiting the adaptive immune system. At the same time, regulatory T cells (Treg) expressing CTLA-4 can be induced in peripheral blood and lymph nodes, which can inhibit other immune cells and lead to immune tolerance of the immune system to tumor.

The phagocytosis of tumor-associated macrophages (TAM) in the tumor microenvironment is inhibited. The reason is that almost all tumor cells highly express CD47 protein on the surface, which can bind to the signal regulatory protein α (SIRPα) on the surface of bone marrow cells and send out "don't eat me" or "self" signals to the body, thus inhibiting phagocytosis. CD47, also known as integrin-associated protein (TAP), is a widely expressed transmembrane glycoprotein belonging to the immunoglobulin (Ig) superfamily. The molecular weight of CD47 is 50 kD, containing a large number of glycosylated N-terminal IgV variable domains, five highly hydrophobic transmembrane domains and a short C-terminal cytoplasmic tail. The four selective splicing forms of the C-terminal cytoplasmic tail determine the expression of CD47 in different tissues. The corresponding SIRPα, also known as SHPS-1, BIT or CD172a protein, is a transmembrane protein that is mainly expressed on myeloid cells, including macrophages, myeloid dendritic cells, granulocytes, mast cells and their precursor cells. SIRPα is composed of three extracellular Ig-like domains and four cytoplasmic tyrosine residues, which are presumed to be phosphorylation sites. After phosphorylation, SIRPα activates downstream signaling pathways by binding to and activating the SH2 domain of SHP-1/2 proteins. The expression of SHP-1 and SHP-2 proteins is tissue-specific, thus SIRPα is a docking protein that recruits and activates downstream protein phosphatases in response to extracellular stimulation. Oldenborg first reported that mature red blood cells (RBC) protect themselves from elimination of splenic macrophages by the binding of CD47 with SIRPα on splenic macrophages. Subsequently, the researchers found that RBC can also bind to SIRPα on monocyte to inhibit Fcγ receptor-dependent phagocytosis, which is achieved by dephosphorylation of myosin-IIA, a key molecule in phagocytosis. Clinically, high expression of CD47 has been found in a variety of solid tumors and hematological malignancies, including acute myeloid leukemia (AML), acute lymphoid leukemia (ALL), chronic myeloid leukemia (CML), non-Hodgkin's lymphoma (NHL), breast cancer, bladder cancer, ovarian cancer, colon cancer, etc. Its essence is that tumor cells escape the cell elimination of macrophages through the regulatory mechanism mentioned above. CD47 also affects other biological processes by binding to other receptors or by signaling through its intracellular cytoplasmic region. Interaction of CD47 with thrombospondin-1 (TSP-1) or vascular endothelial growth factor receptor 2 (VEGFR-2) inhibits angiogenesis, thereby limiting tumor growth.

Many studies have proved that CD47 antibody or SIRPα-Fc recombinant protein can play a role in different mouse PDX models, and the combined use with cytarabine, doxorubicin, paclitaxel, cisplatin and other common chemotherapeutic drugs or rituximab, alemtuzumab, cetuximab, trastuzumab also has a good effect. Sockolosky et al. reported for the first time that the combined use of CD47 nanobodies and PD-L1 shows a good anti-tumor effect in the Syngeneic model of melanoma B16F10 cells. In recent years, several antibodies for CD47-SIRPα pathway have entered clinical phase I, including Hu5F9-G4 (malignant solid tumor: NCT02216409, hematological malignancy: NCT02678338, NCT03248479, colon cancer: NCT02953782, B cell non-Hodgkin's lymphoma: NCT02953509), CC-90002 (AML and myelodysplastic syndrome: NCT02641002, advanced solid tumor and hematological tumor: NCT02367196), SRF231 (advanced solid tumor and hematological tumor: NCT03512340), SIRPα-Fc recombinant protein TTI-662 (solid tumor: NCT02890368, hematological malignancy and solid tumor: NCT02663518, myeloma and lymphoma: NCT03530683), ALX148 (advanced solid tumors and lymphomas: NCT03013218).

The biological function of CD47 determines that CD47 therapeutic antibodies and SIRPα-Fc recombinant proteins may have hematological toxicity or induce the risk of anemia, which has been reported in CD47 gene knockout NOD mice and mouse models treated with CD47 antibody. In addition, CD47 of endothelial cell has been reported to promote transendothelial migration of T cells through cell adhesion interaction with SIRPγ which is mainly expressed in T cells but not myeloid cells.

Therefore, the use of SIRPα antibodies is a better option to block the CD47-SIRPα signaling pathway. The Weissman research group of Stanford University proved that the screened humanized SIRPα antibody KWAR23 combined with rituximab can effectively inhibit the growth of Burkitt lymphoma in SRG mice (Rag2−/−Il2rγ−/−) knocked into human SIRPα gene, but KWAR23 alone had no obvious efficacy.

DISCLOSURE OF THE PRESENT APPLICATION

The object of the present invention is to provide an anti-SIRPα antibody or antigen-binding fragment thereof, and use thereof. The anti-SIRPα antibody or antigen-binding fragment thereof can bind to human SIRPα protein and block CD47-SIRPα signaling pathway.

In order to achieve the above object, the present invention provides an anti-SIRPα antibody or antigen-binding fragment thereof, which comprises: a heavy chain variable region and a light chain variable region; wherein, the heavy chain variable region comprises: VHCDR1, VHCDR2 and VHCDR3 with amino acid sequence as shown in SEQ ID NO: 3, 4 and 5, respectively; the light chain variable region comprises: VLCDR1, VLCDR2 and VLCDR3 with amino acid sequence as shown in any of the following groups;

(1) SEQ ID NO: 37, 38, and 9;
(2) SEQ ID NO: 39, 38, and 9;
(3) SEQ ID NO: 7, 40, and 9;
(4) SEQ ID NO: 7, 8, and 41;
(5) SEQ ID NO: 7, 8, and 42;
(6) SEQ ID NO: 7, 8, and 43;
(7) SEQ ID NO: 37, 38, and 41;
(8) SEQ ID NO: 44, 38, and 41;
(9) SEQ ID NO: 7, 8, and 9.

The sequences of the VLCDRs can be found in the following table:

| Protein number | Light chain plasmid number | VLCDR1 | VLCDR2 | VLCDR3 |
|---|---|---|---|---|
| QP256253 | QD253 | RASKSVSSSGYNYIF (SEQ ID NO: 7) | LASNLDS (SEQ ID NO: 8) | QHSRELPT (SEQ ID NO: 9) |
| QP256279 | QD279 | RASQSVRSSGYNWIF (SEQ ID NO: 37) | LASNRDS (SEQ ID NO: 38) | / |
| QP256291 | QD291 | RASKSVGSSGYNWLF (SEQ ID NO: 39) | LASNRDS (SEQ ID NO: 38) | / |
| QP2561581 | QD1581 | / | LASNLDP (SEQ ID NO: 40) | / |
| QP2561586 | QD1586 | / | / | QESRELPT (SEQ ID NO: 41) |
| QP2561589 | QD1589 | / | / | QESWELPT (SEQ ID NO: 42) |
| OQP2561594 | QD1594 | / | / | QHSRDLPT (SEQ ID NO: 43) |
| QP2561770 | QD1770 | RASQSVRSSGYNWIF (SEQ ID NO: 37) | LASNRDS (SEQ ID NO: 38) | QESRELPT (SEQ ID NO: 41) |
| QP2561771 | QD1771 | RASKSVSSSGYNWIF (SEQ ID NO: 44) | LASNRDS (SEQ ID NO: 38) | QESRELPT (SEQ ID NO: 41) |

Optionally, the variable region further comprises a murine-derived or human-derived FR region.

Optionally, the sequence of the FR region is derived from murine; the sequence of the heavy chain variable region is as shown in SEQ ID NO: 2 or has at least 85% sequence identity thereto, and the sequence of the light chain variable region is as shown in SEQ ID NO: 6 or has at least 85% sequence identity thereto.

Optionally, the human-derived FR region comprises: heavy chain FR region sequences; wherein the heavy chain FR region sequences are derived from combined sequences of human germline heavy chains IGHV1-18 and IGHJ2*01, which comprise FR1, FR2, and FR3 regions of human germline heavy chain IGHV1-18 and a FR4 region of human germline heavy chain IGHJ2*01.

Optionally, the human-derived FR region comprises: light chain FR region sequences; wherein the light chain FR region sequences are derived from combined sequences of human germline light chains IGKV4-1 and IGKJ2*01, which comprise FR1, FR2, and FR3 regions of human germline light chain IGKV4-1 and a FR4 region of human germline heavy chain IGKJ2*01.

Optionally, the FR region sequence of the heavy chain variable region is derived from human germline, and the sequence of the heavy chain variable region is as shown in SEQ ID NO: 17 or has at least 85% sequence identity thereto.

Optionally, the FR region sequence of the light chain variable region is derived from human germline, and the sequence of the light chain variable region is selected from any one of SEQ ID NO: 18, 19, 20, 21, 22, 23, 24, 25, or has at least 85% sequence identity thereto.

Optionally, the anti-SIRPα antibody or the antigen-binding fragment thereof further comprises: a heavy chain constant region selected from human IgG1, IgG2, IgG3, or IgG4 or a variant thereof and a light chain constant region selected from human κ, λ chain or a variant thereof.

Optionally, the heavy chain constant region comprises: a Fc fragment or a variant thereof.

Optionally, the variant of the Fc fragment is derived from IgG1, according to EU Numbering, including mutation sites: L234A, L235A, and K338A.

Optionally, the heavy chain sequence of the anti-SIRPα antibody or the antigen binding fragment thereof is as shown in SEQ ID NO: 26, or has at least 85% sequence identity thereto.

Optionally, the anti-SIRPα antibody or the antigen-binding fragment thereof is a monoclonal antibody, a bispecific antibody, or a multispecific antibody, or the antibody or the antigen-binding fragment thereof is used for preparing an antibody-drug conjugate.

Optionally, the structural form of the anti-SIRPα antibody or the antigen-binding fragment thereof is Fab, F(abs')2, Fv, or ScFv.

The present invention also provides a pharmaceutical composition comprising the above-mentioned anti-SIRPα antibody or antigen-binding fragment thereof, and one or more pharmaceutically acceptable carriers, diluents or excipients.

The present invention also provides a nucleic acid molecule encoding the above-mentioned anti-SIRPα antibody or antigen-binding fragment thereof.

The present invention also provides a vector comprising the above-mentioned nucleic acid molecule.

The present invention also provides a host cell obtained by transformed with the above-mentioned vector.

The present invention also provides the use of the above-mentioned anti-SIRPα antibody or antigen-binding fragment thereof in the manufacture of a medicament for inhibiting or treating a disease, disorder or condition.

Optionally, the medicament is prepared by combining the anti-SIRPα antibody or antigen-binding fragment thereof with one or more other cancer therapeutic agents.

Optionally, the disease, disorder or condition comprises cancer, solid tumor, chronic infection, inflammatory disease, multiple sclerosis, autoimmune disease, neurological disease, brain injury, nerve injury, polycythemia, hemochromatosis, trauma, septic shock, fibrosis, atherosclerosis, obesity, type II diabetes, transplant dysfunction or arthritis.

Optional, the cancer is selected from anal cancer, appendix cancer, astrocytoma, basal cell carcinoma, gallbladder cancer, gastric cancer, lung cancer, bronchial cancer, bone cancer, hepatobiliary cancer, pancreatic cancer, breast cancer, liver cancer, ovarian cancer, testicular cancer, renal cancer, renal pelvis and ureter cancer, salivary gland cancer, small intestine cancer, urethral cancer, bladder cancer, head and neck cancer, spinal cancer, brain cancer, cervical cancer, uterine cancer, endometrial cancer, colon cancer, colorectal cancer, rectal cancer, esophageal cancer, gastrointestinal cancer, skin cancer, prostate cancer, pituitary cancer, vaginal cancer, thyroid cancer, laryngeal cancer, glioblastoma, melanoma, myelodysplastic syndrome, sarcoma, teratoma, chronic lymphocytic leukemia (CLL), chronic myeloid leukemia (CML), acute lymphoblastic leukemia (ALL), acute myeloid leukemia (AML), Hodgkin's lymphoma, non-Hodgkin's lymphoma, multiple myeloma, T or B cell lymphoma, gastrointestinal interstitialoma, soft tissue tumor, hepatocellular carcinoma and adenocarcinoma.

The present invention also provides the use of the above-mentioned anti-SIRPα antibody or antigen-binding fragment thereof in the manufacture of a preparation for blocking the binding of SIRPα and CD47, wherein the preparation comprises a detection agent.

Compared with the prior art, the present invention has the following beneficial effects:

(1) The anti-SIRPα antibody or antigen-binding fragment thereof provided by the present invention can bind to human SIRPα protein, block CD47-SIRPα signaling pathway, and is expected to be used for tumor treatment or preparation of tumor antibody drugs.

(2) The anti-SIRPα antibody or antigen-binding fragment thereof provided by the present invention can bind to all subtypes of human SIRPα protein, which is beneficial to clinical development.

EMBODIMENT FOR THE PRESENT APPLICATION

Figure 1:
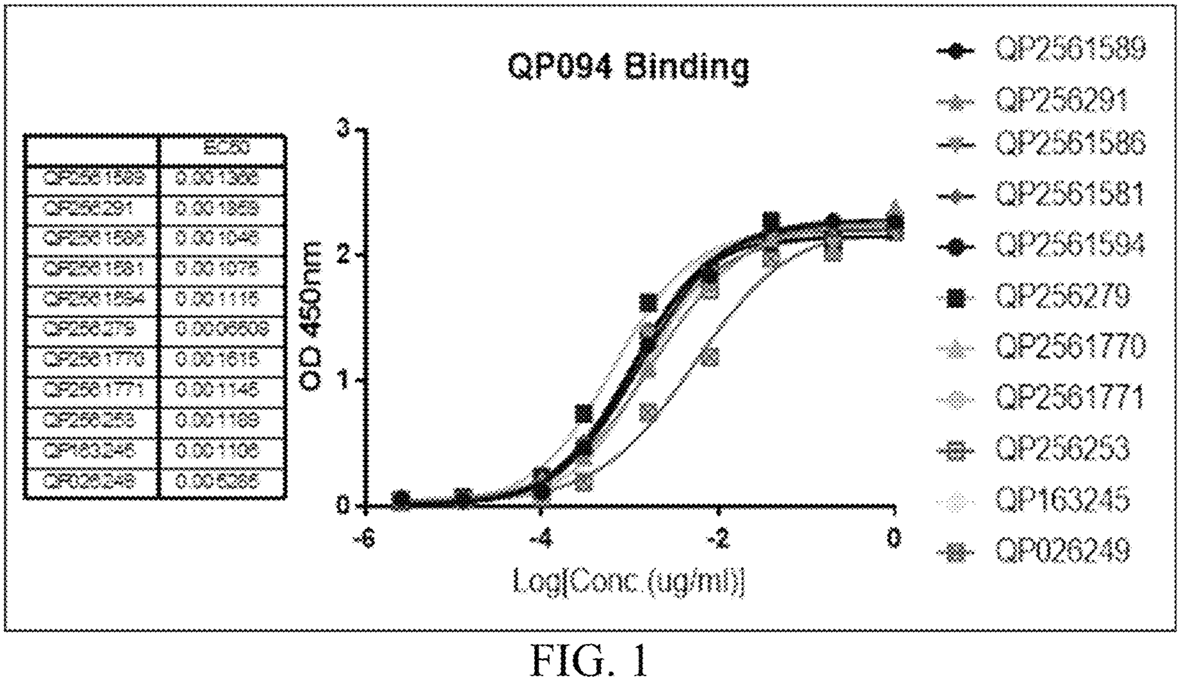
FIGS. 1 to 6 show the results of Binding-ELISA detection.
Figure 2:
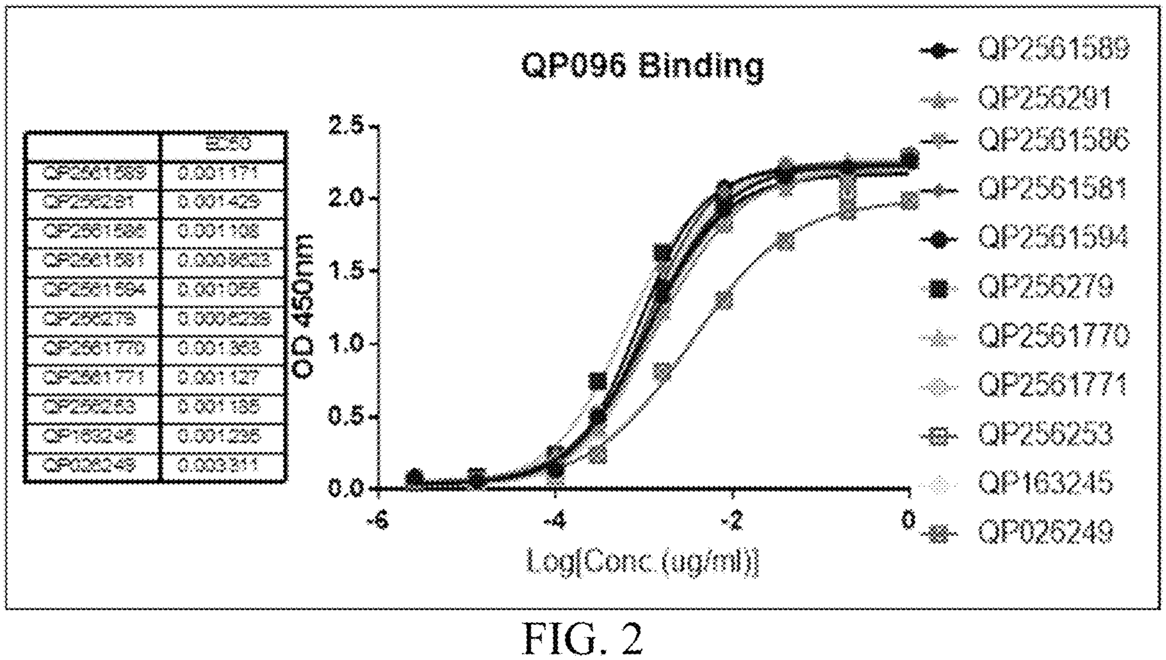
Figure 3:
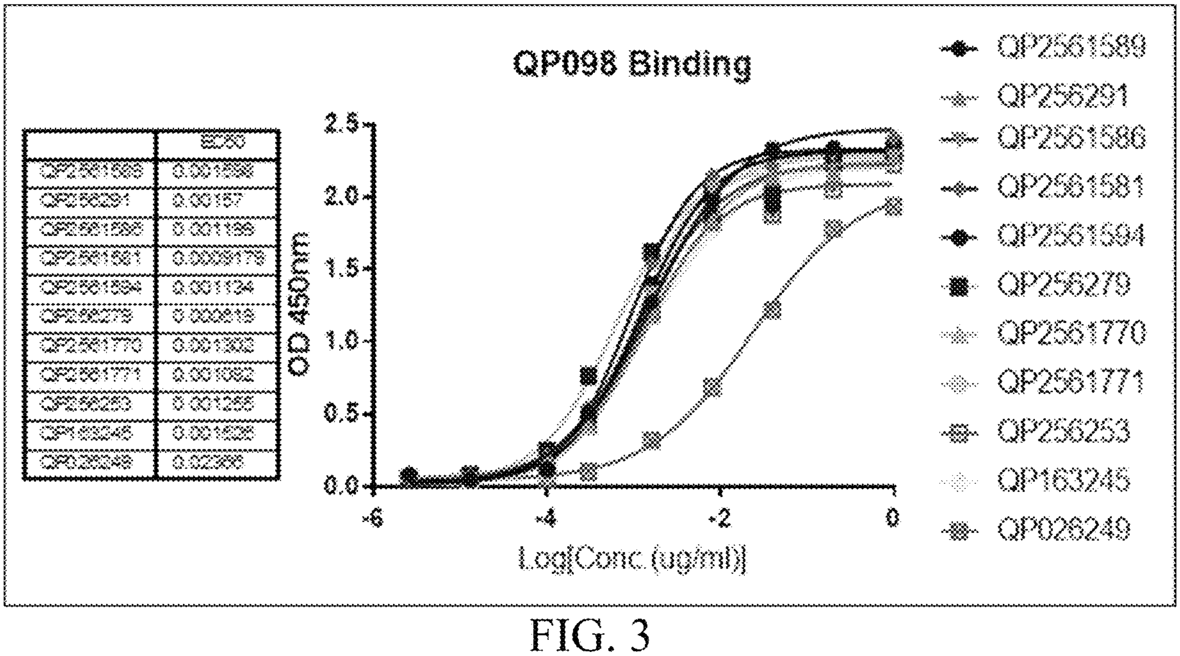
Figure 4:
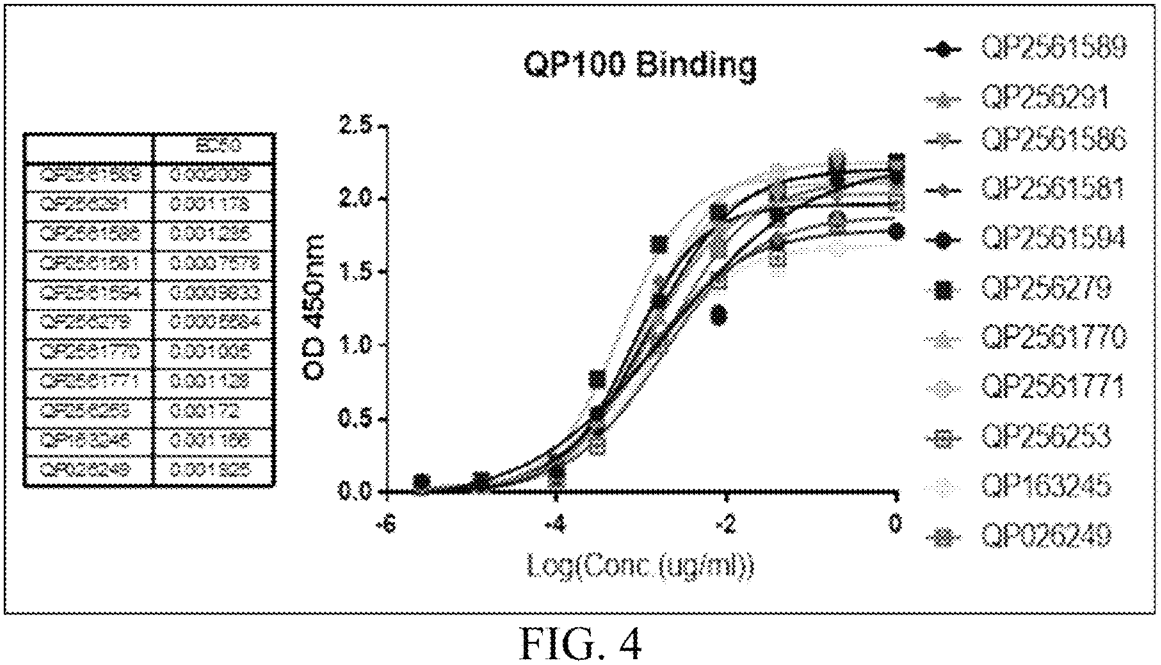
Figure 5:
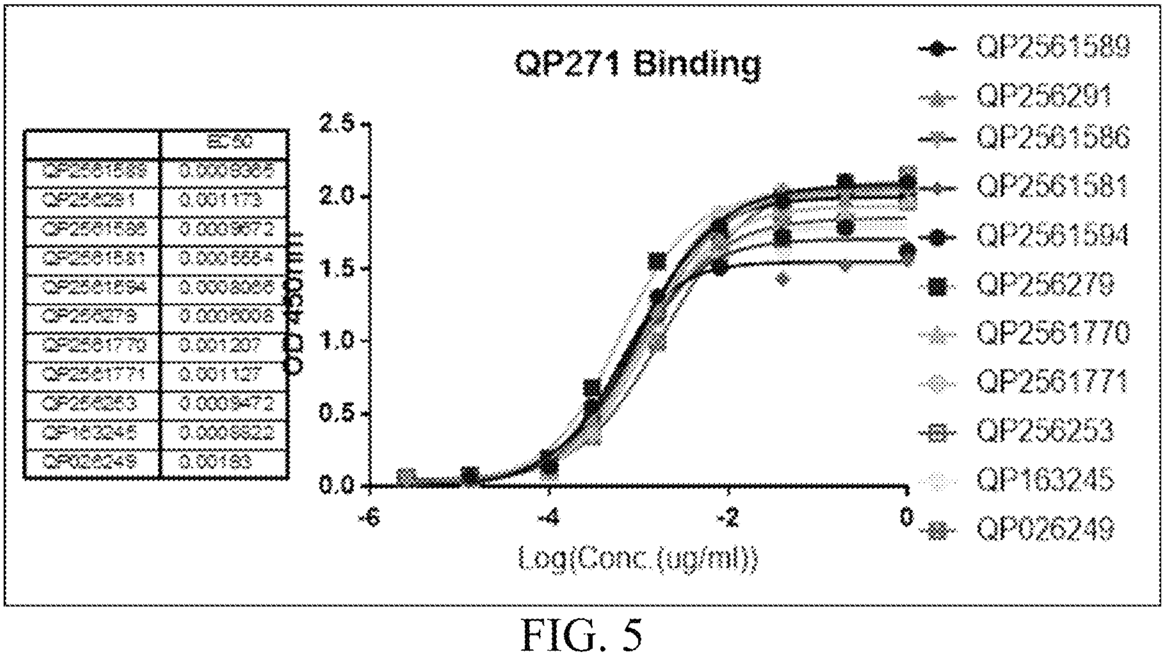
Figure 6:
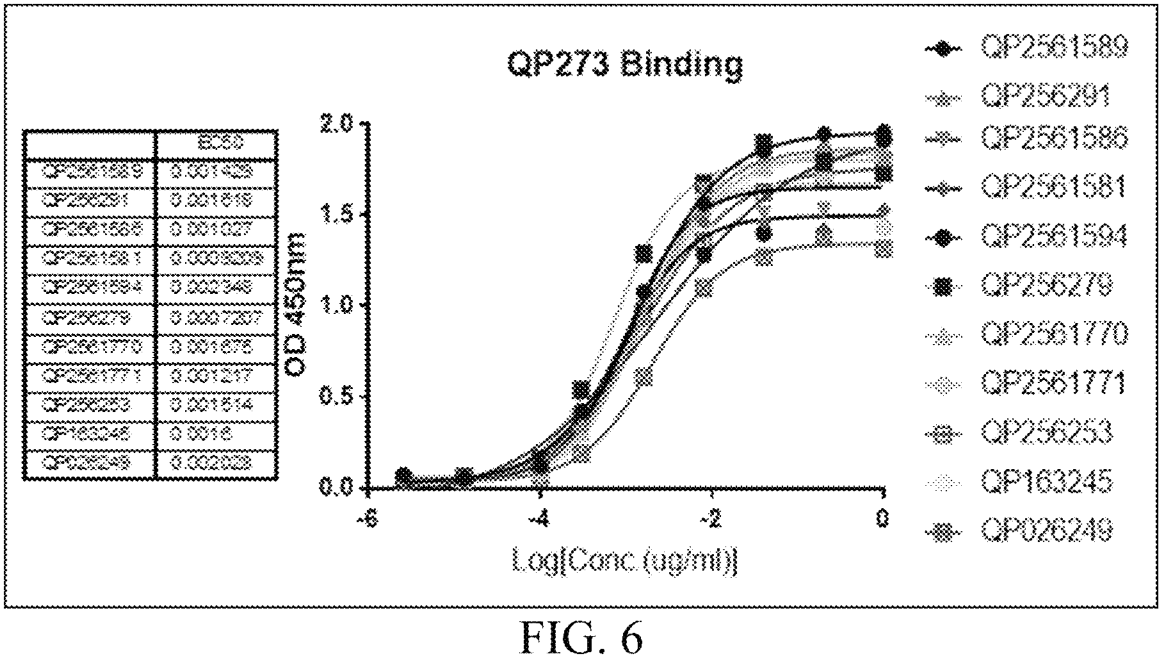

The technical solution of the present invention is further described below with reference to the accompanying drawings and embodiments.

The experimental methods without specific conditions in the experiment are usually in accordance with conventional conditions or conditions recommended by the manufacturer of raw materials or commodities. Reagents without specific source are commercially available conventional reagents.

Term:

An “antibody” (Ab) refers to an immunoglobulin (Ig) that comprises at least one antigen-binding site and is capable of specifically binding to an antigen.

An “antigen” is a substance that can induce immune response in the body and specifically bind to an antibody. The binding of an antibody to an antigen is mediated by interactions formed between the two, including hydrogen bonds, Van der Waals forces, ionic bonds, and hydrophobic bonds. The region on the surface of an antigen to which an antibody binds is an “antigenic determinant” or “epitope”, and in general, there are multiple determinants in an antigen.

The term “antibody” referred in the present invention should be understood in its broadest sense and encompass monoclonal antibodies (including full length monoclonal antibodies), polyclonal antibodies, antibody fragments, multispecific antibodies comprising at least two different antigen binding domains (e.g., bispecific antibodies). An antibody also includes a murine antibody, a humanized antibody, a chimeric antibody, a human antibody, and an antibody from other origins. The antibody of the invention can be derived from any animal, including, but not limited to, immunoglobulin molecules of humans, non-human primates, mice, rats, cows, horses, chickens, camels, llamas, alpacas, guanacos, vicunas, and the like. The antibody may contain additional alterations, such as unnatural amino acids, Fc effector function mutations, and glycosylation site mutations. Antibodies also include post-translationally modified antibodies, fusion proteins comprising antigenic determinants of antibodies, and immunoglobulin molecules comprising any other modification to the antigen recognition site, as long as these antibodies exhibit the desired biological activity.

The basic structure of an antibody is a Y-shaped monomer consisting of two identical heavy chains (H) and two identical light chains (L) linked by disulfide bonds. Each chain is composed of 2 to 5 domains (also known as functional regions) with similar sequences but different functions containing about 110 amino acids. The amino acid sequences of the light chain and the heavy chain near the N-terminus of the antibody molecule vary greatly, and the formed domain is called variable region (V region); the region with relatively constant amino acid sequence near the C-terminus is called constant region (C region).

The V regions of heavy chain and light chain are called VH and VL, respectively. There are three regions in VH and VL with highly variable composition and arrangement of amino acids, called hypervariable regions (HVR). These regions form a spatial conformation complementary to the antigen epitope, which are also called complementarity determining regions (CDR). Three CDRs of VH are represented by VHCDR1, VHCDR2, and VHCDR3 respectively, and three CDRs of VL are represented by VLCDR1, VLCDR2, and VLCDR3 respectively. The six CDRs of VH and VL together constitute an antigen-binding site. The diversity of amino acids in CDRs is the molecular basis for the specific binding of antibodies to a large number of different antigens. The composition and arrangement of amino acids other than CDRs in the V region relatively have little change and are called frame regions or framework regions (FR). VH and VL each have four framework regions, which are represented by FR1, FR2, FR3, and FR4, respectively. Each VH and VL is composed of three CDRs and four FRs, arranged from amino-terminus to carboxyl-terminus in the following order: FR1, CDR1, FR2, CDR2, FR3, CDR3, FR4.

According to the amino acid sequence of the heavy chain constant region of the antibody, human immunoglobulins can be divided into five classes: IgM, IgG, IgA, IgD, and IgE. It can be further divided into different subclasses (isotypes), e.g., human IgG can be divided into IgG1, IgG2, IgG3, IgG4; IgA can be divided into IgA1 and IgA2. No subclasses of IgM, IgD, and IgE have been found. Light chains can be classified into kappa chains and lambda chains according to their amino acid sequences. The antibodies of the present invention may be of any class (e.g., IgM, IgG, IgA, IgD, IgE) or subclass (e.g., IgG1, IgG2, IgG3, IgG4, IgA1, IgA2).

The constant regions of the heavy and light chains are referred to as CH and CL, respectively. The heavy chain constant region of IgG, IgA and IgD has three domains of CH1, CH2 and CH3, and the heavy chain constant region of IgM and IgE has four domains of CH1, CH2, CH3 and CH4.

The region between CH1 and CH2 is a hinge region, which is rich in proline, so it is easy to stretch and bend, and can change the distance between the two Y-shaped arms, which is conducive to the simultaneous binding of the two arms to the epitopes.

An “antigen-binding fragment” refers to a Fab fragment, a F(abs')2 fragment, a Fv fragment, a ScFv fragment, or the like having antigen-binding activity. A “Fab fragment” (fragment of antigen binding, Fab) refers to an antibody fragment consisting of VL, VH, CL and CH1 domains, which binds to a single epitope (monovalent). Those skilled in the art know that papain hydrolyzes IgG to form two identical Fab segments and one Fc segment; pepsin hydrolyzes IgG to form one F(abs')2 segment and several polypeptide fragments (pFc'). If the disulfide bond between F(abs')2 heavy chains is broken, two Fab' fragments can be formed, and the latter can be further enzymatically hydrolyzed into Fv fragments. An Fv fragment contains a heavy chain variable region and a light chain variable region of the antibody, but no constant region. Single chain variable fragment (scFv), or single chain antibody, is formed by linking the heavy chain variable region and light chain variable region of the antibody through a linking fragment (linker).

The terms “Fc”, “Fc segment” or “Fc fragment” refer to a crystallizable fragment, which has no antigen binding activity and is the interaction site of an antibody with an effector molecule or a cell surface Fc receptor (FcR). The Fc fragment comprises the constant region polypeptides of the antibody other than the heavy chain constant region CH1. Fc fragments bind to cells with corresponding Fc receptors on their surface, resulting in different biological effects. In ADCC effect (antibody-dependent cell-mediated cytotoxicity), the Fab segment of the antibody binds to the antigen epitope of virus-infected cells or tumor cells, and its Fc segment binds to the FcR on the surface of killer cells (NK cells, macrophages, etc.) to mediate the direct killing of target cells by killer cells. ADCP refers to antibody-dependent cellular phagocytosis, and the mechanism of ADCP is that the target cells acted by antibodies activate the FcγR on the surface of macrophages, induce phagocytosis, make the target cells internalized and degraded by phagosome acidification. Elimination of antibody Fc function is more beneficial in certain specific situations. These situations include the use of antibodies as: (1) receptor agonists, inducing cellular signaling; (2) receptor antagonists, blocking the binding of receptor and ligand, and inhibiting signaling; or, (3) drug carriers to deliver drugs to target cells expressing the corresponding antigen. If the Fc function is maintained, it will cause the antibody drug to accidentally injure cells expressing the corresponding receptor, and cause the antibody conjugate drug to accidentally injure important immune cells in the case of off-target.

The combination of Fc variants or mutations is not limited to the following formats (according to the EU Numbering).

| IgG | FC Mutate(EU numbing) |
|---|---|
| IgG1 | L234A, L235A<br>L234A, L235A, P329G<br>L234F, L235E, P331S<br>D265A, N297A<br>L234F, L235E, N297A<br>L234F, L235E, D265A<br>L234A, L235E, P331S<br>L234A, L235E, N297A<br>L234A, L235E, D265A<br>L234A, L235A, P331S<br>L234A, L235A, N297A<br>L234A, L235A, D265A<br>L235E, D265A, P331S<br>L235E, N297A, P331S<br>L235E, N297A<br>L235A, D265A, P331S<br>L235A, N297A, P331S<br>N297Q<br>N297A<br>N297G<br>A287C, N297G, L306C<br>R292C, N297G, V302C |
| hIgG4 | IS228P, L235E, P329G<br>S228P, L235E<br>S228P, F234A, L235E<br>S228P, F234A, L235A |
| IgG2m4 | ASTKGPSVFPLAPCSRSTSESTAALGCLVKDYFPEPVTVS<br>WNSGALTSGVHTFPAVLQSSGLYSLSSVVTVPSSNFGTQT<br>YTCNVDHKPSNTKVDKTVERKCCVECPPCPAPPVAGPSVF<br>LFPPKPKDTLMISRTPEVTCVVVDVSQEDPEVQFNWYVDG<br>VEVHNAKTKPREEQFNSTYRVVSVLTVLHQDWLNGKEYKC<br>KVSNKGLPSSIEKTISKAKGQPREPQVYTLPPSQEEMTKN<br>QVSLTCLVKGFYPSDIAVEWESNGQPENNYKTTPPVLDSD<br>GSFFLYSRLTVDKSRWQEGNVFSCSVMHEALHNHYTQKSL<br>SLSLGK (SEQ ID NO: 62)<br>N297A<br>N297Q<br>N297G. |

The CDR amino acid residues of the antibody or antigen-binding fragment of the present invention conform in number and position to the known Kabat numbering rule.

At present, murine antibodies are a major source of antibody drugs. Because of their immunogenicity, murine antibodies are generally humanized. The following examples provide murine antibodies, chimeric antibodies, and humanized antibodies. A "chimeric antibody" is an antibody obtained by fusing variable regions of a murine antibody with constant regions of a human antibody, and it can reduce the immune response induced by the murine antibody. The constant regions of the human antibody may be selected from the heavy chain constant region of human IgG1, IgG2, IgG3, IgG4 or variants thereof, and the light chain constant region of human kappa, lambda chain or variants thereof. The "humanized antibody" refers to an antibody obtained by transplanting CDR sequences of a murine antibody into a human antibody variable region framework, and it can overcome the strong reaction induced by a chimeric antibody due to carrying a large number of mouse protein components. Such framework sequences can be obtained from public DNA databases or published references including germline antibody gene sequences. In order to avoid the reduced activity caused by the decrease of immunogenicity, the human antibody variable region framework sequence can be subjected to a minimum of reverse mutation or back mutation to maintain the activity.

Theoretically, the improvement of antibody affinity can contribute to improve the specificity and efficacy of antibodies, reduce the dose of drugs, and reduce toxic side effects, etc. Although actual research work has proved that the relationship between the improvement of affinity and the improvement of antibody titer is not always linear, especially in the treatment of solid tumors, in many cases this linear relationship is obvious. The humanized antibody of the present invention also includes a humanized antibody in which CDRs are further subjected to affinity maturation by phage display. The theoretical basis of antibody affinity maturation in vitro is to mimic the process of antibody affinity in vivo. By constructing a random mutation library to simulate the high frequency mutation of B cells in vivo, high affinity antibodies can be screened.

The drugs provided herein may contain a "therapeutically effective amount" of the antibody or antigen-binding fragment. A "therapeutically effective amount" refers to an amount of a therapeutic agent effective to prevent or ameliorate a particular disease and may vary depending on multiple factors such as the disease state, age, and weight of the patient, and the ability of the agent to produce a desired therapeutic effect in different patients.

"Sequence identity" refers to the sequence similarity between two polynucleotide sequences or between two polypeptides, and the degree to which two polynucleotides or two polypeptides have the same bases or amino acids. As used herein, "having at least 85% sequence identity" refers to achieving at least 85%, 90%, 95%, 97%, or 99% identity.

Antibody-Drug Conjugates (ADCs) refer to binding proteins linked to one or more chemical drugs, which optionally may be therapeutic or cytotoxic agents. An antibody-drug conjugate can be obtained by linking the cytotoxic small molecule (cytotoxin) and the antibody via a permanent or labile chemical linker. ADCs can selectively and sustainably deliver cytotoxic drugs to tumors.

The gene encoding SIRPα is a polymorphic gene, and 10 variants of SIRPα are known in the human population. Katsuto Takenaka et al. sequenced the IgV-encoding SIRP alpha domain of 37 unrelated normal Caucasians, Africans, Chinese, and Japanese from the Human HapMap Genome Project and found 10 different SIRP alpha IgV-encoding alleles (Polymorphism in Sirpa modulates engraftment of human hematopoietic stem cells, NATURE IMMUNOLOGY VOLUME 8 NUMBER 12 Dec. 2007). The 10 SIRPα variants are SIRPα V1/V2/V3/V4/V5/V6/V7/V8/V9/V10 subtypes, respectively. Although SIRPalpha is highly polymorphic, the amino acid sequence alignment of known human SIRPalpha alleles by Chia Chi M. Ho et al showed that there are only two unique sequences at the CD47 binding interface of SIRPalpha, which are allele V1 (a2d1) and V2 (a1d1). ("Velcro" Engineering of High Affinity CD47 Ectodomain as Signal Regulatory Protein (SIRP alpha) Antagonists That Enhance Antibody-dependent Cellular Phagocytosis, JOURNAL OF BIOLOGICAL CHEMISTRY, VOLUME 290·NUMBER 20·May 15, 2015).

Figure 24:
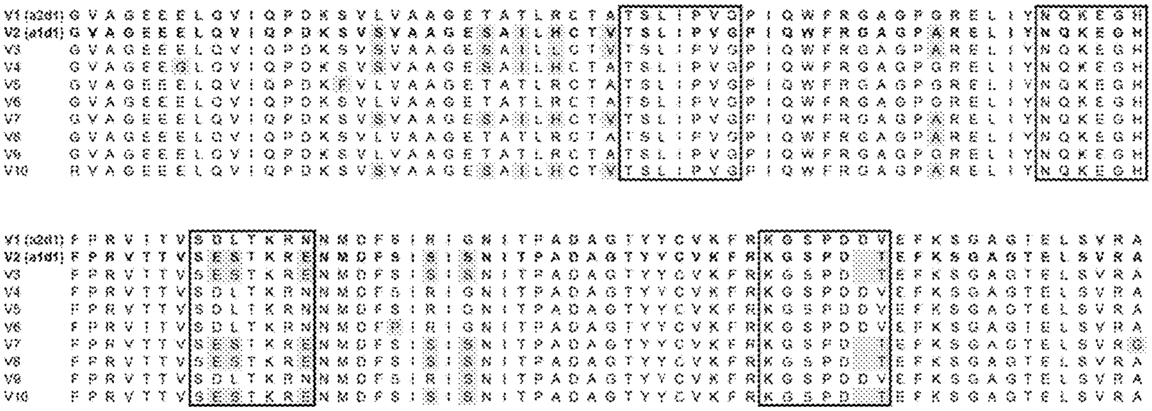
FIG. 24 shows the amino acid sequence alignment of the known human SIRP alpha-binding domain alleles. The amino acid sequences of V1 to V10 are as shown in SEQ ID NOs: 51 to 60.

As shown in FIG. 24, the amino acid sequence alignment of known human SIRP alpha binding domain alleles shows only two variations at the CD47-contact interface: a1d1 and a2d1. The first line of text in FIG. 24 is the amino acid sequence of the most significant human SIRP alpha allele V1 (a2d1), and the second line of text in FIG. 1 is the amino acid sequence of the most significant human SIRP allele V2 (a1d1). Black boxes indicate residues that interact with CD47, while shading parts indicate residues that differ from the V1 sequence. Sanger sequencing of SIRPα sequences from 2535 individuals and 510 samples by Janet Sim et al. identified two SIRPα variants v1 and v2, representing three allelic groups: homozygous v1/v1, homozygous v2/v2, and heterozygous v1/v2. The distribution and frequency of SIRPα v1 and v2 allelic groups were determined in different populations and unrelated subpopulations. The distributions of v1/v2 heterozygotes in 5 super populations Europe (EUR), America (AMR), East Asia (EAS), Africa (AFR) and South Asia (SAS) are similar, ranging from 42.0% to 47.2%. The number of v2/v2 in East Asian population is significantly higher than v1/v1, with the occurrence frequencies of 42.3% and 13.3%, respectively. The number of v1/v1 in African, European, American and South Asian population is higher than v2/v2, and the occurrence frequencies of v1 and v2 are 30.3-49.1% and 8.9-24.2%, respectively (see MABS, 2019, VOL. 11, NO. 6, 1036 "C1052, https://doi.org/10.1080/19420862.2019.1624123). Aduro Biotech also studied that the occurrence frequency of v2/v2 homozygotes in East Asian population is 41.3% and that of v1/v1 homozygotes is 34.6%, which also proves that 41.3% of East Asian population are V2/V2 homozygotes (see Voets et al. Journal for ImmunoTherapy of Cancer (2019) 7:340).

Based on the results of the SIRPα polymorphism analysis, the ability of anti-SIRPα antibodies to simultaneously bind to both SIRPα v1 and SIRPα v2 genes is critical for clinical development.

Example 1: Obtaining Anti-SIRPα Mouse Antibodies (1) Immunization of Mice:

Anti-human SIRPα monoclonal antibodies were generated by immunizing mice. Experimental Balb/c white mice, female, 6 weeks old. Feeding environment: SPF level. After purchase, the mice were kept in laboratory environment for 1 week, with 12/12 hours light/dark cycle adjustment, at the temperature of 20-25 °C, and humidity of 40-60%. Balb/c mice were immunized with recombinant protein QP009 (SIRPα) 50 μg/mouse for the first time with complete Freund's adjuvant (CFA). Two weeks later, the mice were alternately immunized with QP009 (SIRPα) in incomplete Freund's adjuvant (IFA) or QP009 (SIRPα) in aluminum salt Alum+CpG ODN 1826 at 25 μg/mouse once a week.

QP009 (SIRPα) has the amino acid sequence shown below (SEQ ID NO:1):

EEELQVIQPDKSVLVAAGETATLRCTATSLIPVG-PIQWFRGAGPGRELIYNQKEGHFPRVT TVSDLTKRNNMDFSIRIGNIT-PADAGTYYCVKFRKGSPDDVEFKSGAGTELSVRAK-PSDYKD DDDK HHHHHH. The sequence is referenced from UNIPROT number P78324 (31-149) (SIRPA—Tyrosine-protein phosphatase non-receptor type substrate 1 precursor—*Homo sapiens* (Human)—SIRPA gene & protein (uniprot.org)).

(2) Cell Fusion:

Mice with high antibody titers in serum were selected for spleen cell fusion. 72 hours prior to fusion, the selected mice were rush immunized by intraperitoneal injection. Spleen lymphocytes were fused with myeloma Sp2/0 cells using an optimized PEG-mediated fusion procedure to obtain hybridoma cells. The fused hybridoma cells were resuspended in HAT complete medium (IMDM medium containing 20% FBS, 1×HAT and 1×OPI), subpackaged in 96-well cell culture plates ($1\times10^5$/150 μl/well), cultured at 37 °C and 5% $CO_2$. On the 5$^{th}$ day after fusion, IMDM medium (containing 2×HAT and 1×OPI) containing 20% FBS was added at 50 μl/well, and cultured at 37 °C, 5% $CO_2$. On the 7$^{th}$ to 8$^{th}$ day after fusion, according to the cell growth density, the whole medium was changed with 250 μl/well, and cultured at 37 °C, 5% $CO_2$, wherein the culture medium was HT complete medium (IMDM medium containing 20% FBS, 1×HT and 1×OPI).

(3) Screening of Hybridoma Cells:

According to the cell growth density, 10-14 days after fusion, ELISA detection was performed to screen the anti-SIRPα antibody in the hybridoma supernatant. The supernatant of hybridoma fusion wells was taken and primarily screened by ELISA in whole 96-well plate, and the anti-SIRPα antibodies in the supernatant that were detected blocking the binding of SIRPα/CD47 were the primary screening positive wells. Then, the supernatant of the primary screening positive wells was taken to detect the binding to QP009 (SIRPα) by ELISA, and the clones that are positive for binding to SIRPα and blocking the binding of SIRPα/CD47 were selected, i.e., the anti-SIRPα antibody positive clone wells. The positive clones were expanded and transferred to the 24/6 wells plate in time, and the cell culture supernatant was detected again by ELISA, and those clone wells positive for binding to SIRPα and blocking the binding of SIRPα/CD47 were the anti-SIRPα antibody positive clone wells. The positive clones were subjected to 2-3 rounds of limited dilution to single-cell clones, and the positive single-cell strain was cryopreserved to obtain single-cell clone 71C10.

(4) Sequencing of Hybridoma Monoclonal Antibody to Obtain Antibody Sequence:

The positive hybridoma monoclonal cell line 71C10 was taken and mRNA of that was extracted. The mRNA was reverse transcribed into cDNA, and the cDNA was used as a template for PCR amplification. PCR positive clones were selected for sequencing, and the sequences of the light and heavy chain variable regions of monoclonal antibody were obtained by sequence analysis.

The sequence of heavy chain variable region of 71C10 is SEQ ID NO: 2, as follows:

QVQLQQPGTELVRPGASVKLSCKASGYTFTNYWINWVKQRPGQGLEWIA
MIDPSDSETHYNQIFKDKATLTVDKSSNTAYMQLSSLTSGDSAVYYCAM
DYGSLYAMDYWGRGTSVTVSS.

Note: The order is FR1-CDR1-FR2-CDR2-FR3-CDR3-FR4. The bold and underlined parts are VHCDR1 (SEQ ID NO: 3), VHCDR2 (SEQ ID NO: 4), and VHCDR3 (SEQ ID NO: 5), respectively.

The sequence of light chain variable region of 71C10 is SEQ ID NO: 6, as follows:

DIVLTQSPASLAVSLGQRATISCRASKSVSSSGYNYIFWYQQKPGQPPK
LLIYLASNLDSGVPARFSGSGSGTDFTLNIHPVEEEDAATYYCQHSREL
PTFGGGTKLEIK.

Note: The order is FR1-CDR1-FR2-CDR2-FR3-CDR3-FR4. The bold and underlined parts are VLCDR1 (SEQ ID NO: 7), VLCDR2 (SEQ ID NO: 8), and VLCDR3 (SEQ ID NO: 9), respectively.

Example 2: Affinity Detection of Anti-SIRPα Chimeric Antibody by SPR (1) The murine variable region sequences of 71C10 monoclonal cell line were fused with human constant region gene to obtain chimeric antibody molecules. The antibody light chain employs a kappa light chain constant region CL.

At the same time, different antigen sequences were designed for the performance test of antibody molecules. The molecular clone designs of antigens and chimeric antibodies are shown in Table 1 and Table 2.

TABLE 1

Molecular clone designs of chimeric antibodies

| Protein number | Plasmid number | Sequence number | Description | Origin |
|---|---|---|---|---|
| QP026027 | QD026 | SEQ ID NO: 10 | pQDK-KWAR23-L | |
| | QD027 | SEQ ID NO: 11 | pQDH-KWAR23-H | |
| QP026249 | QD026 | SEQ ID NO: 10 | pQDK-KWAR23-L | |
| | QD249 | SEQ ID NO: 12 | pQDH-KWAR23-H (IgG4) | |
| QP163164 | QD163 | SEQ ID NO: 13 | pQDK-180122 VL | 71C10 |
| | QD164 | SEQ ID NO: 14 | pQDH-180122 VH | |
| QP163245 | QD163 | SEQ ID NO: 13 | pQDK-180122 VL | |
| | QD245 | SEQ ID NO: 15 | pQDH-180122 VH (IgG4) | |

Note:
Antibodies with protein numbers QP026027 and QP026249 are used as control antibodies, both of which adopt the variable region sequences of the known anti-SIRPα antibody KWAR23 and are different in the constant regions. The variable regions of monoclonal cell line 71C10 are used in QP163164 and QP163245, and the difference is that the constant regions are different.

The sequences shown by the above sequence numbers give the heavy and light chain sequences of each antibody molecule, respectively.

pQD is the name of the vector with the signal peptide and constant region gene (CH1-FC/CL) fragment, wherein pQDH is used for the connection and expression of the heavy chain variable region, and has the signal peptide and constant region gene (CH1-FC) fragment; and pQDK is used for the connection and expression of the light chain variable region, and has the signal peptide and constant region gene (CL) fragment. "H" represents a heavy chain and "L" represents a light chain. "(IgG4)" represents that the heavy chain adopts the constant region of human IgG4. If "(IgG4)" is not indicated, the constant region of human IgG1 is used by default. 180122VH represents the heavy chain variable region derived from the monoclonal cell line 71C10, and 180122VL represents the light chain variable region derived from the monoclonal cell line 71C10.

Exemplarily, "pQDH-KWAR23-H" represents that the control sequence KWAR23 is fused to the pQDH vector, wherein pQDH carries a signal peptide and a constant region gene (CH1-FC) fragment and uses the constant region of human IgG1. "pQDH-180122VH" represents that the heavy chain variable region sequence 180122VH is fused to the pQDH vector, using the constant region of human IgG1. The sequences shown in the above sequence numbers are as follows:

>QD026

(SEQ ID NO: 10)

MDMRVPAQLLGLLLLWFPGSRCQIVLTQSPAIMSASPGEKVTLTCSASSSVSSSYLYWY

QQKPGSSPKLWIYSTSNLASGVPARFSGSGSGTSYSLTISSMEAEDAASYFCHQWSSYPRTFG

AGTKLELKRTVAAPSVFIFPPSDEQLKSGTASVVCLLNNFYPREAKVQWKVDNALQSGNSQ

ESVTEQDSKDSTYSLSSTLTLSKADYEKHKVYACEVTHQGLSSPVTKSFNRGEC.

>QD027

(SEQ ID NO: 11)

MEFGLSWLFLVAILKGVQCEVQLQQSGAELVKPGASVKLSCTASGFNIKDYYIHWVQQ

RTEQGLEWIGRIDPEDGETKYAPKFQDKATITADTSSNTAYLHLSSLTSEDTAVYYCARWGAY

WGQGTLVTVSSASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSFFLYSKLTVDKSR

WQQGNVFSCSVMHEALHNHYTQKSLSLSPGK. Wherein, MEFGLSWLFLVAILKGVQC (SEQ ID NO: 63)

is the signal peptide.

>QD249

(SEQ ID NO: 12)

MEFGLSWLFLVAILKGVQCEVQLQQSGAELVKPGASVKLSCTASGFNIKDYYIHWVQQ

RTEQGLEWIGRIDPEDGETKYAPKFQDKATITADTSSNTAYLHLSSLTSEDTAVYYCARWGAY

WGQGTLVTVSSASTKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESKYGPPCPPCPAPEF

LGGPSVFLFPPKPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLYSRLTVDKSRWQE

-continued

GNVFSCSVMHEALHNHYTQKSLSLSLGK. Wherein, MEFGLSWLFLVAILKGVQC (SEQ ID NO: 63) is the signal peptide.

>QD163

(SEQ ID NO: 13)

DIVLTQSPASLAVSLGQRATISCRASKSVSSSGYNYIFWYQQKPGQPPKLLIYLASNLDSG VPARFSGSGSGTDFTLNIHPVEEEDAATYYCQHSRELPTFGGGTKLEIKRTVAAPSVFIFPPSD EQLKSGTASVVCLLNNFYPREAKVQWKVDNALQSGNSQESVTEQDSKDSTYSLSSTLTLSK ADYEKHKVYACEVTHQGLSSPVTKSENRGEC. Wherein, the double underlined part is the constant region sequence.

>QD164

(SEQ ID NO: 14)

QVQLQQPGTELVRPGASVKLSCKASGYTFTNYWINWVKQRPGQGLEWIAMIDPSDSET HYNQIFKDKATLTVDKSSNTAYMQLSSLTSGDSAVYYCAMDYGSLYAMDYWGRGTSVTVS SASTKGPSVFPLAPSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPCPAPELLGGPSVFL FPPKPKDTLMISRTPEVTCVVVDVSHEDPEVKFNWYVDGVEVHNAKTKPREEQYNSTYRV VSVLTVLHQDWLNGKEYKCKVSNKALPAPIEKTISKAKGQPREPQVYTLPPSRDELTKNQVS LTCLVKGFYPSDIAVEWESNGQPENNYKTTPPVLDSDGSFFLYSKLTVDKSRWQQGNVFSCS VMHEALHNHYTQKSLSLSPGK. Wherein, the double underlined part is the constant region sequence.

>QD245

(SEQ ID NO: 15)

MEFGLSWLFLVAILKGVQCQVQLQQPGTELVRPGASVKLSCKASGYTFTNYWINWVK QRPGQGLEWIAMIDPSDSETHYNQIFKDKATLTVDKSSNTAYMQLSSLTSGDSAVYYCAMD YGSLYAMDYWGRGTSVTVSSASTKGPSVFPLAPCSRSTSESTAALGCLVKDYFPEPVTVSWN SGALTSGVHTFPAVLQSSGLYSLSSVVTVPSSSLGTKTYTCNVDHKPSNTKVDKRVESKYGPP CPPCPAPEFLGGPSVFLFPPKPKDTLMISRTPEVTCVVVDVSQEDPEVQFNWYVDGVEVHNA KTKPREEQFNSTYRVVSVLTVLHQDWLNGKEYKCKVSNKGLPSSIEKTISKAKGQPREPQV YTLPPSQEEMTKNQVSLTCLVKGFYPSDIAVEWESNGQPENNYKTTPPVLDSDGSFFLYSRLT VDKSRWQEGNVFSCSVMHEALHNHYTQKSLSLSLGK.

Wherein,

MEFGLSWLFLVAILKGVQC (SEQ ID NO: 63)is the signal peptide, and the double underlined part is the heavy chain constant region sequence.

TABLE 2

Clone designs of antigens

| | Protein number | Plasmid number | Sequence number | Description |
|---|---|---|---|---|
| Antigen expression and production | QP094 | QD094 | SEQ ID NO: 45 | pQD-human SIRPα V1 ECD (E31-R370)-flag-his |
| | QP096 | QD096 | SEQ ID NO: 46 | pQD-human SIRPα V2 ECD (E31-R370)-flag-his |
| | QP098 | QD098 | SEQ ID NO: 47 | pQD-cyno SIRPα (I7G9Z7) ECD (E31-R369)-flag-his |
| | QP100 | QD100 | SEQ ID NO: 48 | pQD-cyno SIRPα (G7PGS8) ECD (E29-R368)-flag-his |
| | QP271 | QD271 | SEQ ID NO: 49 | pQD-rhesusSIRPα1-flag-his T-557-28 |
| | QP273 | QD273 | SEQ ID NO: 50 | pQD-cynoSIRPα2-flag-his T-557-14 |

Note:

QP098 is cynomolgus SIRPα sequence (Uniprot database sequence number I7G9Z7), QP100 is cynomolgus SIRPα sequence (Uniprot database sequence number G7PGS8), QP271 is rhesus monkey SIRPα sequence, which is obtained by the inventor through sequencing monkey PBMC, QP273 is cynomolgus SIRPα sequence, which is obtained by the inventor through sequencing monkey PBMC.

(2) Expression and Purification of Antigen and Chimeric Antibody

The culture density of 293E cells was maintained at (0.2-3)×$10^6$/ml, and a maintenance phase medium (GIBCO Freestyle 293 expression medium) was used for culture; the cells to be transfected were centrifuged one day before transfection, the medium was replaced, and the cell density was adjusted to (0.5-0.8)×$10^6$/ml. On the day of transfection, the cell density of 293E cells was (1-1.5)×$10^6$/ml. The plasmids and the transfection reagent PEI were prepared. The amount of plasmids to be transfected was 100 m/100 ml cells, and the mass ratio of PEI to plasmid used was 2:1. The plasmids and PEI were mixed uniformly, then standing for 15 min (should not exceed 20 min). The mixture of plasmids and PEI was slowly added to 293E cells, and cultured in a shaker at 8% $CO_2$, 120 rpm and 37 °C. On the fifth day of transfection, the cell supernatant was collected after being centrifuged in a horizontal centrifuge at 4700 rpm for 20 min.

Protein A affinity chromatography purification: At least 3CV (actual volume 20 ml) of balance solution was allowed to pass through the column, so as to ensure that the pH and conductivity of the final solution flowing out of the instrument are consistent with the balance solution, and the flow rate was 1 ml/min; the culture supernatant after centrifugation was allowed to pass through the column, 40 ml of sample was loaded, and the flow rate was 0.33 ml/min; at least 3CV (actual volume 20 ml) of balance solution was allowed to pass through the column, so as to ensure that the pH and conductivity of the final solution flowing out of the instrument are consistent with the balance solution, and the flow rate was 0.33 ml/min; the eluent was allowed to pass through the column, and the elution peaks (PAC-EP) began to be collected when the UV280 increased to 15 mAU; and collection stopped when the UV280 decreased to 15 mAU, and the flow rate was 1 ml/min. After the sample collection was completed, the PAC-EP was adjusted to neutral with a pH adjustment solution.

(3) Affinity Detection by Surface Plasmon Resonance (SPR)

The affinity of the anti-SIRPα chimeric antibody QP163164 to human SIRPα V1 (protein number QP094) and human SIRPα V2 (protein number QP096) was determined by Biacore T200 (GE). Tables 3 and 4 show the detection results of QP163164 and QP026027. The results show that the SIRPα chimeric antibody QP163164 binds to human SIRPα V1 with a KD of 5.27E-10M, and binds to human SIRPα V2 with a KD of 6.78E-10M. The binding affinity to human SIRPα V1 and human SIRPα V2 is significantly better than the control antibody KWAR23 (QP026027).

TABLE 3

Affinity of anti-SIRPα chimeric antibodies to SIRPα V1 and SIRPα V2

| | SIRPα V1 (QP094) | | | SIRPα V2 (QP096) | | |
|---|---|---|---|---|---|---|
| Number | ka (1/Ms) | kd (1/s) | KD (M) | ka (1/Ms) | kd (1/s) | KD (M) |
| QP163164 | 2.71E+06 | 1.43E−03 | 5.27E−10 | 3.39E+06 | 2.30E−03 | 6.78E−10 |
| QP026027 | 9.08E+05 | 4.65E−03 | 5.12E−09 | 2.01E+06 | 2.46E−02 | 1.23E−08 |

The affinity of the chimeric antibodies to cynomolgus SIRPα determined by biacore is as shown in the following table:

TABLE 4

Affinity of chimeric antibodies to cynomolgus SIRPα

| | Cynomolgus SIRPα (QP100) | | |
|---|---|---|---|
| Number | ka (1/Ms) | kd (1/s) | KD (M) |
| QP163164 | 1.99E+06 | 2.63E−01 | 1.32E−07 |
| QP026027 | 3.13E+06 | 1.99E−02 | 6.35E−09 |

Example 3: Humanization of Anti-SIRPα Hybridoma Monoclonal Antibodies

By means of aligning the IMGT germline gene database of the heavy and light chain variable regions of human antibody and using MOE software, the heavy and light chain variable region germline genes having high homology with QP163164 were selected as templates, and the CDRs of murine antibodies were grafted into the corresponding human templates to form a variable region sequence in the order of FR1-CDR1-FR2-CDR2-FR3-CDR3-FR4. Then, some important amino acid residues were selected for reverse mutation combinations. Among them, the amino acid residues were identified and annotated by Kabat numbering system. In the following examples, the heavy chain FR region sequences are derived from the combined sequences of human germline heavy chains IGHV1-18 and IGHJ2*01, which comprise the FR1, FR2, FR3 regions of human germline heavy chain IGHV1-18 and the FR4 region of human germline heavy chain IGHJ2*01. The light chain FR region sequences are derived from the combined sequences of human germline light chains IGKV4-1 and IGKJ2*01, which comprise the FR1, FR2, FR3 regions of human germline light chain IGKV4-1 and the FR4 region of human germline light chain IGKJ2*01.

(1) Cloning of Anti-SIRPα Antibody Humanized Molecules

Primers were designed for PCR to construct VH/VK gene fragments of various humanized antibodies, and then homologous recombination was carried out with the expression vector pQD having a signal peptide and a constant region gene (CH1-FC/CL) fragments to construct the antibody full-length expression vector VH-CH1-FC-pQD/VK-CL-pQD.

The online software DNAWorks (v3.2.2) (http://helixweb.nih.gov/dnaworks/) was used to design a number of primers to synthesize VH/VK containing the gene fragment needed for recombination: 5'-30 bp signal peptide+VH/VK+30 bp CH1/CL-3'. According to the operating instructions of Primer STAR GXL DNA polymerase of TaKaRa, VH/VK containing the gene fragment needed for recombination was obtained by two-step PCR using the multiple primers designed above. Construction and enzyme digestion of expression vector pQD: the characteristic of a number of restriction enzymes, such as BsmBI, that their recognition sequences differ from the digestion sites was used to design and construct the expression vector pQD. The vector was digested using BsmBI enzyme, and the gel was cut and recovered for later use. Construction of heavy chain expression vector pQD-VH-CH1-FC and light chain expression vector pQD-VL-CL: heavy chain variable region VH gene fragments were mixed with BsmBI-digested vector pQD (with a signal peptide and a heavy chain constant region (CH1-FC) fragment) at a ratio of 3:1; light chain variable region VL gene fragments were mixed with BsmBI-digested vector pQD (with a signal peptide and a light chain constant region (CL) fragment) at a ratio of 3:1; the mixtures were transferred into DH5a competent cells respectively, then subjected to ice bath at 0 °C for 30 min, heat shock at 42 °C for 90 s, then added with 5 times of LB medium, incubated at 37 °C for 45 min, coated to LB-Amp plate, and cultured overnight at 37 °C, and single clones were picked for sequencing to obtain individual clones of interest.

The specific information of the humanization design for QP163164 is shown in the Table below. The protein expression number is QP256253. In this table, a kappa light chain constant region CL is employed for the antibody light chain, and a human IgG4 constant region is employed for the antibody heavy chain (see Example 2 for the specific sequences of constant regions). The humanized design light and heavy chain variable region sequences are not limited to the sequences shown in the following table.

TABLE 5

Humanized design light and heavy chain sequences and protein expression number

| | Protein number | Heavy chain plasmid number | Sequence number | Description | Light chain plasmid number | Sequence number | Description |
|---|---|---|---|---|---|---|---|
| QP163164 humanized clone | QP256253 | QD256 | SEQ ID NO: 17 | pQDH (IgG4)-164_VH.1B | QD253 | SEQ ID NO: 16 | pHrK-164_VL.1A |

Note:
The light chain variable region of QP256253 is encoded by the plasmid numbered QD253.

The specific sequence of light chain variable region SEQ ID NO:16 is:

DIVLTQSPDSLAVSLGERATINCRASKSVSSSGYNYIFWYQQKPGQPPK LLIYLASNLDSGVPDRFSGSGSGTDFTLTISSLQAEDVAVYYCQHSREL PTFGQGTKLEIK.

The heavy chain variable region of QP256253 is encoded by the plasmid numbered QD256. The specific sequence of heavy chain variable region SEQ ID NO:17 is:

QVQLVQSGAEVKKPGASVKVSCKASGYTFTNYWINWVRQAPGQGLEWIA MIDPSDSETHYNQIFKDRATLTTDTSTSTAYMELRSLRSDDTAVYYCAM DYGSLYAMDYWGRGTLVTVSS.

(2) Expression of Humanized Anti-SIRPα Antibody Proteins

The culture density of 293E cells was maintained between $(0.2\text{-}3)\times10^6$/ml, and a maintenance phase medium (GIBCO Freestyle 293 expression medium) was used for culture; the cells to be transfected were centrifuged one day before transfection, the medium was replaced, and the cell density was adjusted to $(0.5\text{-}0.8)\times10^6$/ml. On the day of transfection, the cell density of 293E cells was $(1\text{-}1.5)\times10^6$/ml. The plasmid and transfection reagent PEI were prepared, the amount of plasmid to be transfected was 100m/100 ml cells, and the mass ratio of PEI to the plasmid as used was 2:1. The plasmid and PEI were mixed uniformly, then allowed to stand for 15 min (should not exceed 20 min). The mixture of plasmids and PEI was slowly added to 293E cells, and cultured in a shaker at 8% $CO_2$, 120 rpm and 37 °C. On the fifth day of transfection, the cell supernatant was collected by centrifugation at 4700 rpm for 20 min in a horizontal centrifuge.

(3) Purification of Anti-SIRPα Antibody Humanized Protein

Protein A affinity chromatography purification: At least 3CV (actual volume 20 ml) of balance solution was allowed to pass through the column, so as to ensure that the pH and conductivity of the final solution flowing out of the instrument are consistent with the balance solution, and the flow rate was 1 ml/min; the culture supernatant after centrifugation was allowed to pass through the column, 40 ml of sample was loaded, and the flow rate was 0.33 ml/min; at least 3CV (actual volume 20 ml) of balance solution was allowed to pass through the column, so as to ensure that the pH and conductivity of the final solution flowing out of the instrument are consistent with the balance solution, and the flow rate was 0.33 ml/min; the eluent was allowed to pass through the column, and the elution peaks (PAC-EP) began to be collected when the UV280 increased to 15 mAU; and collection stopped when the UV280 decreased to 15 mAU, and the flow rate was 1 ml/min. After the sample collection was completed, the PAC-EP was adjusted to neutral with a pH adjustment solution.

(4) Identification of Humanized SIRPα Antibody Activity (Binding-ELISA)

Binding-ELISA experimental method: The plate was coated with QP094 (SIRPαV1-flag-his), QP096 (SIRPαV2-Flag-his), and QP100 (cynoSIRPα-flag-his) at 0.5 μg/ml, 50 μl/well, respectively, for 4 °C overnight. The plate was washed with PBS for 3 times, added with 3% BSA/PBS at 200 μl/well, and incubated at RT for 2 h, then washed with PBST for 3 times. Antibodies with different concentrations were added, and incubated for 1 h at RT, then the plate was washed with PBST for 3 times and with PBS for 3 times. Secondary antibody HRP-anti Fab diluted at 1:2500 was added and incubated at RT for 1 h, then the plate was washed with PB ST for 3 times and with PBS for 3 times. TMB was used to develop and 2M $H_2SO_4$ was used to terminate, and reading was performed at 450 nm.

(5) Identification of Humanized SIRPα Antibody Affinity by SPR

The affinity of the humanized antibody to human SIRPα V1, human SIRPα V2 and cynomolgus SIRPα was determined by Biacore. The results are as shown in Table 6 below. The results show that the anti-SIRPα humanized antibody QP256253 binds to human SIRPα V1 with a KD value of 3.36E-10M, and binds to human SIRPα V2 with a KD value of 3.19E-10M.

TABLE 6

| Affinity of the humanized antibody to human SIRPα V1 and SIRPα V2 and cynomolgus SIRPα | | | | | | | | | |
|---|---|---|---|---|---|---|---|---|---|
| | QP094 (human SIRPα V1) | | | QP096 (human SIRPα V2) | | | QP100 (cyno SIRPα) | | |
| Number | ka (1/Ms) | kd (1/s) | KD (M) | ka (1/Ms) | kd (1/s) | KD (M) | ka (1/Ms) | kd (1/s) | KD (M) |
| QP256253 | 2.35E+06 | 7.90E−04 | 3.36E−10 | 3.42E+06 | 1.09E−03 | 3.19E−10 | 2.52E+06 | 1.96E−01 | 7.79E−08 |

Example 4: Affinity Maturation of Anti-SIRPα Antibody QP163164

(1) Construction of Humanized Phagemid Vector

Humanized QP256253 was constructed into a phagemid vector in scFv mode (VH-3×GGGGS (SEQ ID NO: 64)-VL) as the wild-type sequence (i.e., as the original or initial sequence, and the sequences obtained by affinity maturation screening were mutant sequences). VH, (GGGGS (SEQ ID NO: 64)) 3 linker, and VL were spliced by over-lap PCR, and were ligated into phagemid vectors via NcoI and NotI restriction sites.

(2) Construction of Phage Display Library

The constructed wild-type scFv was used as a template, and codon-based primers were used. In the process of primer synthesis, there was 50% wild-type codon and 50% NNK (reverse primer: MNN) in the codon of the mutation region, and the mutation library was constructed by introducing mutations into all CDR regions. The PCR fragment was digested by NcoI and NotI enzymes, ligated into the phagemid vector, and finally electrotransformed into *E. coli* TG1. Each codon-based primer was used to establish an independent library.

(3) Library Screening

After the library was rescued to package the phage particles for screening, biotinylated QP098 (cynoSIRPα (ECD)) antigen and streptavidin magnetic beads were used for liquid phase screening, and the antigen concentration was reduced in each round of screening relative to that in the previous round. After three rounds of screening, 250 clones were picked for phage ELISA detection of binding activity, and the positive clones were sequenced. After alignment analysis of the sequenced clones and removal of redundant sequences, the non-redundant sequences were converted into full-length IG (CH1-CH2-CH3 of hIgG4 was selected for heavy chain constant region; kappa(κ) light chain CL was selected for light chain constant region) for expression in mammalian cells. Full length IG protein was obtained after affinity purification. The specific sequence is shown in the table below. In this table, a kappa light chain constant region CL is employed for the antibody light chain, and a human IgG4 constant region is employed for the antibody heavy chain (see Example 2 for the specific sequences of constant regions).

TABLE 7

| Sequences of positive clones | | | | | |
|---|---|---|---|---|---|
| | Protein number | Heavy chain plasmid number | Sequence number | Light chain plasmid number | Sequence number |
| QP163164 affinity maturation | QP256279 | QD256 | SEQ ID NO: 17 | QD279 | SEQ ID NO: 18 |
| | QP256291 | QD256 | SEQ ID NO: 17 | QD291 | SEQ ID NO: 19 |

TABLE 7-continued

| Sequences of positive clones | | | | |
|---|---|---|---|---|
| Protein number | Heavy chain plasmid number | Sequence number | Light chain plasmid number | Sequence number |
| QP2561581 | QD256 | SEQ ID NO: 17 | QD1581 | SEQ ID NO: 20 |
| QP2561586 | QD256 | SEQ ID NO: 17 | QD1586 | SEQ ID NO: 21 |
| QP2561589 | QD256 | SEQ ID NO: 17 | QD1589 | SEQ ID NO: 22 |
| QP2561594 | QD256 | SEQ ID NO: 17 | QD1594 | SEQ ID NO: 23 |
| QP2561770 | QD256 | SEQ ID NO: 17 | QD1770 | SEQ ID NO: 24 |
| QP2561771 | QD256 | SEQ ID NO: 17 | QD1771 | SEQ ID NO: 25 |

Note:

The naming rule of protein number is the combination of heavy chain plasmid number and light chain plasmid number. Exemplarily, the antibody molecule whose protein number is QP256279 has a heavy chain plasmid number of QD256 and a light chain plasmid number of QD279.

The sequences represented by the sequence numbers in the table are heavy chain variable region or light chain variable region sequences of different antibodies. The specific sequences of light chain variable regions are as follows:

>QD279

(SEQ ID NO: 18)

DIVLTQSPDSLAVSLGERATINCRASQSVRSSGYNWIFWYQQKPGQPPK LLIYLASNRDSGVPDRFSGSGSGTDFTLTISSLQAEDVAVYYCQHSREL PTFGQGTKLEIK.

>QD291

(SEQ ID NO: 19)

DIVLTQSPDSLAVSLGERATINCRASKSVGSSGYNWLFWYQQKPGQPPK LLIYLASNRDSGVPDRFSGSGSGTDFTLTISSLQAEDVAVYYCQHSREL PTFGQGTKLEIK.

>QD1581

(SEQ ID NO: 20)

DIVLTQSPDSLAVSLGERATINCRASKSVSSSGYNYIFWYQQKPGQPPK LLIYLASNLDPGVPDRFSGSGSGTDFTLTISSLQAEDVAVYYCQHSREL PTFGQGTKLEIK.

>QD1586

(SEQ ID NO: 21)

DIVLTQSPDSLAVSLGERATINCRASKSVSSSGYNYIFWYQQKPGQPPK LLIYLASNLDSGVPDRFSGSGSGTDFTLTISSLQAEDVAVYYCQESREL PTFGQGTKLEIK.

>QD1589

(SEQ ID NO: 22)

DIVLTQSPDSLAVSLGERATINCRASKSVSSSGYNYIFWYQQKPGQPPK LLIYLASNLDSGVPDRFSGSGSGTDFTLTISSLQAEDVAVYYCQESWEL PTFGQGTKLEIK.

-continued

>QD1594

(SEQ ID NO: 23)

DIVLTQSPDSLAVSLGERATINCRASKSVSSSGYNYIFWYQQKPGQPPK
LLIYLASNLDSGVPDRFSGSGSGTDFTLTISSLQAEDVAVYYCQHSRDL
PTFGQGTKLEIK.

>QD1770

(SEQ ID NO: 24)

DIVLTQSPDSLAVSLGERATINCRASqSVrSSGYNwIFWYQQKPGQPPK
LLIYLASNrDSGVPDRFSGSGSGTDFTLTISSLQAEDVAVYYCQeSREL
PTFGQGTKLEIK.

>QD1771

(SEQ ID NO: 25)

DIVLTQSPDSLAVSLGERATINCRASKSVSSsGYNwIFWYQQKPGQPPK
LLIYLASNrDSGVPDRFSGSGSGTDFTLTISSLQAEDVAVYYCQeSREL
PTFGQGTKLEIK.

The above bold and underlined parts are VLCDR1, VLCDR2, VLCDR3 of each antibody molecule, respectively, and the comparison with the wild-type sequence QP256253 is as follows:

TABLE 8

Comparison of LCDR region sequences of each antibody molecule with wild-type sequences

| Protein number | Light chain plasmid number | VLCDR1 | VLCDR2 | VLCDR3 |
|---|---|---|---|---|
| QP256253 | QD253 | RASKSVSSSGYNYIF (SEQ ID NO: 7) | LASNLDS (SEQ ID NO: 8) | QHSRELPT (SEQ ID NO: 9) |
| QP256279 | QD279 | RAS**Q**SV**R**SSGYN**W**IF (SEQ ID NO: 37) | LASN**R**DS (SEQ ID NO: 38) | / |
| QP256291 | QD291 | RASKSV**G**SSGYN**WL**F (SEQ ID NO: 39) | LASN**R**DS (SEQ ID NO: 38) | / |
| QP2561581 | QD1581 | / | LASNLD**P** (SEQ ID NO: 40) | / |
| QP2561586 | QD1586 | / | / | Q**E**SRELPT (SEQ ID NO: 41) |
| QP2561589 | QD1589 | / | / | Q**E**S**W**ELPT (SEQ ID NO: 42) |
| OQP2561594 | QD1594 | / | / | QHSR**D**LPT (SEQ ID NO: 43) |
| QP2561770 | QD1770 | RAS**Q**SV**R**SSGYN**W**IF (SEQ ID NO: 37) | LASN**R**DS (SEQ ID NO: 38) | Q**E**SRELPT (SEQ ID NO: 41) |
| QP2561771 | QD1771 | RASKSVSSSGYN**W**IF (SEQ ID NO: 44) | LASN**R**DS (SEQ ID NO: 38) | Q**E**SRELPT (SEQ ID NO: 41) |

Note:
"/" indicates that the sequence is the same as QP256253, and bold indicates different amino acids from QD253.

(4) ELISA Assay

Binding-ELISA experimental method: The plate was coated with QP094 (SIRPαV1-flag-his), QP096 (SIRPαV2-Flag-his), QP098 (cynoSIRPα-flag-his), and QP100 (cynoSIRPα-flag-his) at 0.5 μg/ml, 50 μl/well, respectively, for 4 °C overnight. The plate was washed with PBS for 3 times, added with 3% BSA/PBS at 200 μl/well, and incubated at RT for 2 h, then washed with PBST for 3 times. Antibodies with different concentrations were added, and incubated for 1 h at RT, then the plate was washed with PBST for 3 times and with PBS for 3 times. Secondary antibody HRP-anti Fab diluted at 1:2500 was added and incubated at RT for 1 h, then the plate was washed with PBST for 3 times and with PBS for 3 times. TMB was used to develop and 2M $H_2SO_4$ was used to terminate, and reading was performed at 450 nm. The EC50 values are shown in the table below. The following table also shows the detection results of humanized antibody QP256253, chimeric antibody QP163245, and control antibody QP026249. The results are shown in FIGS. 1 to 6.

TABLE 9

| EC50 values detected by ELISA | | | | | | |
|---|---|---|---|---|---|---|
| conc.(μg/ml) | QP094 | QP096 | QP098 | QP100 | QP271 | QP273 |
| QP2561589 | 0.001366 | 0.001171 | 0.001598 | 0.002009 | 0.0009365 | 0.001429 |
| QP256291 | 0.001859 | 0.001429 | 0.00157 | 0.001178 | 0.001173 | 0.001618 |
| QP2561586 | 0.001046 | 0.001108 | 0.001199 | 0.001235 | 0.0009672 | 0.001027 |
| QP2561581 | 0.001075 | 0.0008623 | 0.0009179 | 0.0007578 | 0.0005554 | 0.0009209 |
| QP2561594 | 0.001115 | 0.001055 | 0.001134 | 0.0009833 | 0.0008066 | 0.002348 |
| QP256279 | 0.0006508 | 0.0006239 | 0.000619 | 0.0005584 | 0.0006008 | 0.0007207 |
| QP2561770 | 0.001615 | 0.001363 | 0.001302 | 0.001005 | 0.001207 | 0.001675 |
| QP2561771 | 0.001145 | 0.001127 | 0.001082 | 0.001128 | 0.001127 | 0.001217 |
| QP256253 | 0.001189 | 0.001185 | 0.001255 | 0.00172 | 0.0009472 | 0.001514 |
| QP163245 | 0.001106 | 0.001235 | 0.001526 | 0.001166 | 0.0008822 | 0.0016 |
| QP026249 | 0.005285 | 0.003311 | 0.02366 | 0.001925 | 0.00193 | 0.002028 |

Figure 7:
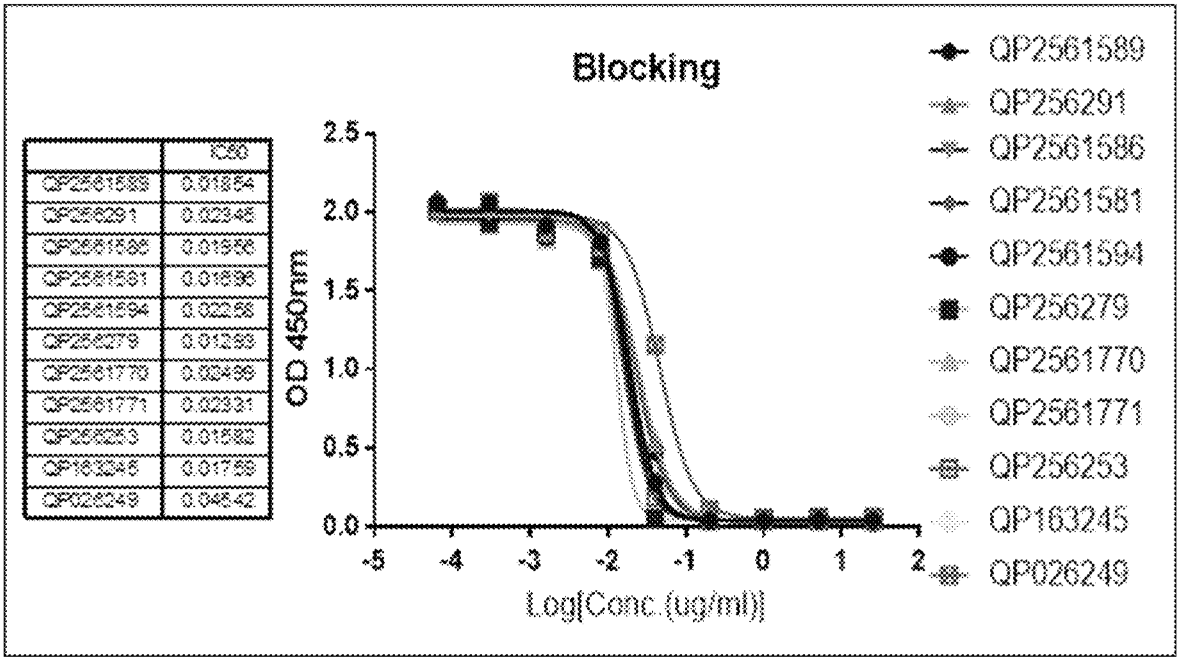
FIG. 7 shows the result of Blocking-ELISA detection.

Blocking-ELISA experimental method: the plate was coated with QP001.2 at 2 μg/ml for 4 °C overnight, washed with PBS for 3 times, and blocked with 5% milk at 250 μl/well. Biotin-QP002 0.05 μg/ml+Abs 50 μg/ml were mixed at 1:1 and incubated at 25 °C for 1 h with HRP-Strepavidin (1:5000). The results are shown in FIG. 7.

(5) Affinity Detection by Surface Plasmon Resonance (SPR)

The affinity of the anti-SIRPα antibodies to human SIRPα V1 type, human SIRPα V2 type and cynomolgus SIRPα was determined by Biacore, and some of the results are shown in Table 10. As shown in Table 10, the anti-SIRPα antibodies QP2561589, QP2561586, QP2561581, QP256279, and QP2561770 all bind to human SIRPα V1 type and human SIRPα V2 type. At the same time, QP2561589, QP2561586, QP256279, QP2561770, QP256253 all bind to different cynomolgus and rhesus monkey SIRPα proteins.

TABLE 10

| Results of Affinity detected by SPR | | | | | |
|---|---|---|---|---|---|
| | Biacore (KD/M) | | | | |
| Protein | QP094 (Human SIRP αV1) | QP096 (Human SIRP αV2) | QP098 (cynomolgus SIRPα) | QP271 (rhesus monkey SIRPα) | QP273 (cyno-molgus SIRPα) |
| QP2561589 | 8.50E−11 | 3.92E−11 | 6.03E−09 | 2.41E−09 | 3.20E−09 |
| QP2561586 | 5.97E−11 | 8.91E−11 | 4.22E−09 | 1.74E−09 | 2.22E−09 |
| QP2561581 | 1.37E−10 | 1.76E−10 | / | / | / |
| QP256279 | 3.54E−11 | 4.46E−11 | 1.56E−09 | 4.41E−10 | 9.18E−10 |
| QP2561770 | 2.88E−11 | 3.68E−11 | 2.56E−10 | 1.00E−10 | 1.63E−10 |
| QP256253 | 2.60E−10 | 2.76E−10 | 2.68E−08 | 7.97E−09 | 1.27E−08 |
| QP163245 | 3.86E−10 | 5.58E−10 | / | / | / |
| QP026249 | 3.43E−09 | 1.36E−08 | 2.71E−08 | / | / |

As can be seen from the above table, the affinity of the affinity mature antibodies QP2561589, QP2561586 and QP256279 proteins for human SIRPα V1 and SIRPα V2 is more than 50 times higher than that of the control antibody KWAR23 (QP026249).

Example 5: FACS Detection of Anti-SIRPα Antibody Binding to Human Renal Clear Cell Adenocarcinoma Cells 786-O Cells Naturally Expressing Human SIRPα

Figure 8:
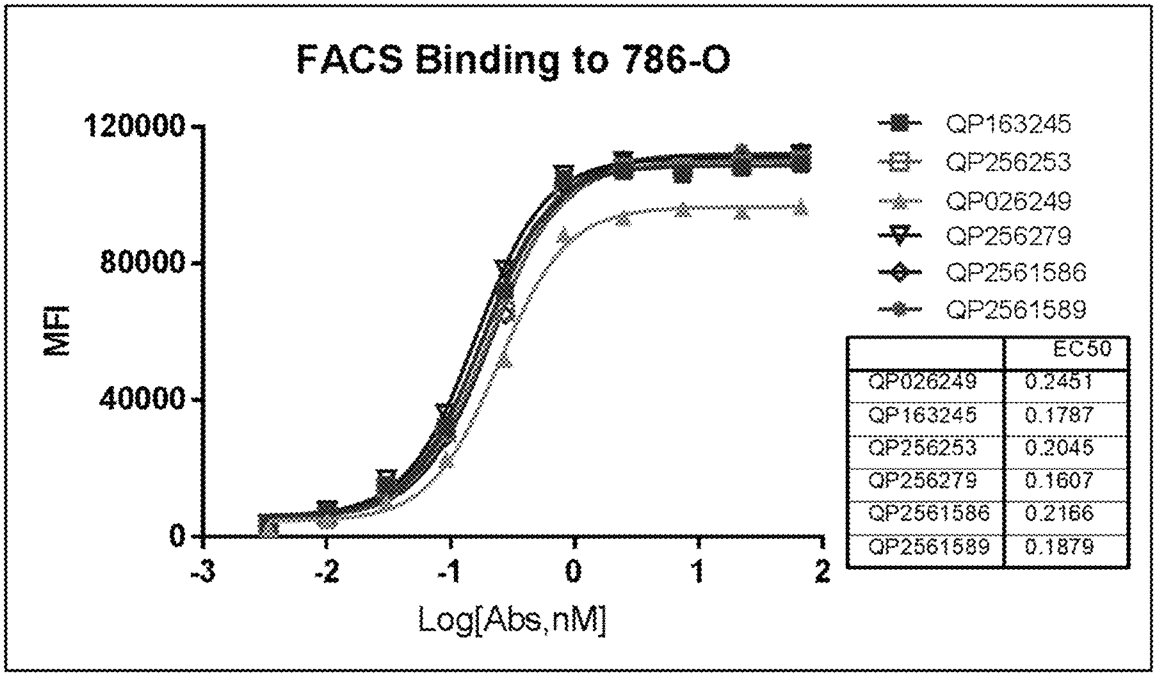
FIG. 8 shows the results of FACS detection of SIRPα antibody binding to human renal clear cell adenocarcinoma cell 786-O cells naturally expressing human SIRPα.

Experimental steps: 786-O cells were collected at 2E5 cells/well, washed with PBS once, then centrifuged at 300 g for 3 min and the supernatant was discarded. Blocking: the cells were resuspended with 2% FBS and were seeded into 96-well U bottom plate with 2E5/well, 200 μl/well, then subjected to ice bath for 1 h. Centrifugation was performed at 300 g for 3 min, and the supernatant was discarded. Antibody incubation: 10 μg/ml antibodies for incubation were diluted at 1:3, 100 μl/well, and subjected to ice bath for 1 h. Centrifugation was performed, and the supernatant was discarded. Pre-cooled PBS was added at 200 μl/well, centrifuged at 300 g for 5 min to discard supernatant, which was repeated twice. Secondary antibody: PE-anti human FC (1:200) 50 μl/well was subjected to ice bath for 0.5 h. Centrifugation was performed and the supernatant was discarded. Pre-cooled PBS was added at 200 μl/well, centrifuged at 300 g for 5 min to discard supernatant, which was repeated 3 times. The mean fluorescence values were read on FACS. The results are shown in FIG. 8, the anti-SIRP α antibodies QP163245, QP256253, QP256279, QP2561586, QP2561589 all binds to human renal clear cell adenocarcinoma cells 786-0 cells naturally expressing human SIRPα, and the binding affinity is much better than that of the control antibody QP026249 (KWAR23).

Example 6: In Vitro Functional Assay ADCP of Anti-SIRPα Antibody (1) The Anti-SIRPα Antibody was Made into Different IgG Subtypes, and the Molecular Cloning Designs were as Follows:

TABLE 11

| Molecular cloning designs for in vitro functional assay ADCP of anti-SIRPα antibody | | | | | | |
|---|---|---|---|---|---|---|
| | IgG subtype | Protein number | Heavy chain plasmid number | Sequence number | Light chain plasmid number | Sequence number |
| Different subtypes of QP256279 | IgG1 (N297Q) | QP32250279 | QD3225 | SEQ ID NO: 27 | QD279 | SEQ ID NO: 18 |
| | IgG4 (N297Q) | QP32260279 | QD3226 | SEQ ID NO: 28 | QD279 | SEQ ID NO: 18 |

TABLE 11-continued

Molecular cloning designs for in vitro functional assay ADCP of anti-SIRPα antibody

| | IgG subtype | Protein number | Heavy chain plasmid number | Sequence number | Light chain plasmid number | Sequence number |
|---|---|---|---|---|---|---|
| | IgG2 | QP32550279 | QD3255 | SEQ ID NO: 29 | QD279 | SEQ ID NO: 18 |
| | IgG1 (L234A, L235A) | QP32600279 | QD3260 | SEQ ID NO: 30 | QD279 | SEQ ID NO: 18 |
| | IgG1 (L234A, L235A, P329G) | QP32650279 | QD3265 | SEQ ID NO: 31 | QD279 | SEQ ID NO: 18 |
| | IgG1 (L234A, L235A, K338A) | QP32700279 | QD3270 | SEQ ID NO: 26 | QD279 | SEQ ID NO: 18 |
| Different subtypes of QP2561586 | IgG4 (N297Q) | QP32261586 | QD3226 | SEQ ID NO: 28 | QD1586 | SEQ ID NO: 21 |
| | IgG1 (L234A, L235A, K338A) | QP32701586 | QD3270 | SEQ ID NO: 26 | QD1586 | SEQ ID NO: 21 |
| Different subtypes of QP2561589 | IgG4 (N297Q) | QP32261589 | QD3226 | SEQ ID NO: 28 | QD1589 | SEQ ID NO: 22 |
| | IgG1 (L234A, L235A, K338A) | QP32701589 | QD3270 | SEQ ID NO: 26 | QD1589 | SEQ ID NO: 22 |
| Different subtypes of KWAR23 | IgG1 (L234A, L235A, K338A) | QP32680026 | QD3268 | SEQ ID NO: 32 | QD026 | SEQ ID NO: 10 |
| | IgG4 (N297Q) | QP32210026 | QD3221 | SEQ ID NO: 35 | QD026 | SEQ ID NO: 10 |
| Different subtypes of Aduro50A | IgG1 (L234A, L235A, K338A) | QP32713240 | QD3271 | SEQ ID NO: 33 | QD3240 | SEQ ID NO: 36 |
| Different subtypes of QP163164 | IgG1 (N297Q) | QP32220163 | QD3222 | SEQ ID NO: 34 | QD163 | SEQ ID NO: 13 |
| Different subtypes of QP256253 | IgG1 (N297Q) | QP32250253 | QD3225 | SEQ ID NO: 27 | QD253 | SEQ ID NO: 16 |
| | IgG4 (N297Q) | QP32260253 | QD3226 | SEQ ID NO: 28 | QD253 | SEQ ID NO: 16 |

Note:
The naming rule of protein number is the combination of heavy chain plasmid number and light chain plasmid number. The sequence numbers of the heavy chains show the heavy chain sequences of different subtype antibodies. The sequence numbers of light chains show the sequences of light chains or light chain variable regions of different subtype antibodies.

Among them, the specific sequence of the heavy chain of QP32700279 (SEQID NO: 26) is as follows:

QVQLVQSGAEVKKPGASVKVSCKASGYTFTNYWINWVRQAPGQGLEWIA

MIDPSDSETHYNQIFKDRATLTTDTSTSTAYMELRSLRSDDTAVYYCAM

DYGSLYAMDYWGRGTLVTVSSASTKGPSV

FPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKT

HTCPPCPAPEAAGGPSVFLFPPKPKDTLM

ISRTPEVTCVVVDVSHEDPEVKFNWYVDGVEVHNAKTKPREEQYNSTYR

VVSVLTVLHQDWLNGKEYKCKVSNKALPAPIEKTISAAKGQPREPQVYT

LPPSRDELTKNQVSLTCLVKGFYPSDIAV

EWESNGQPENNYKTTPPVLDSDGSFFLYSKLTVDKSRWQQGNVFSCSVM

HEALHNHYTQKSLSLSPGK.

The sequence of the light chain variable region of QP32700279 is shown in SEQ ID NO: 18.

(2) In Vitro Functional Assay ADCP of Anti-SIRPα Antibody

Preparation of macrophages: PBMCs were resuscitated, monocytes were isolated with EasySep™ Human Monocyte Isolation Kit (Stemcell-19359), Human Recombinant M-CSF (final concentration of 50 ng/mL) was added and mixed evenly. Cells were cultured at 37 °C for 6 days to be induced into macrophages, and the cells were collected and counted for later use. Raji cells were labeled with CFSE. Raji cells were resuspended to $2\times10^6$ cells/ml and added to the 96-well plate with macrophages at 50 μl/well ($1\times10^5$/well). Dilution of antibody: Rituximab was diluted to with complete medium, and diluted with 3 times to 9 gradients; anti-SIRPα antibodies were diluted to 20 μg/ml with complete medium; Mixture of Antibody: the diluted two kinds of antibodies were mixed at a ratio of 1:1 in the Combination group, and the antibodies were mixed with equal volume of culture medium in the Rituximab group, then added them into the 96-well plate previously seeded with cells at 50 μl/well and cultured at 37 °C for 2 h; FACS detection: phagocytosis was measured by gating live CFSE+/CD14+ cells.

Figure 9:
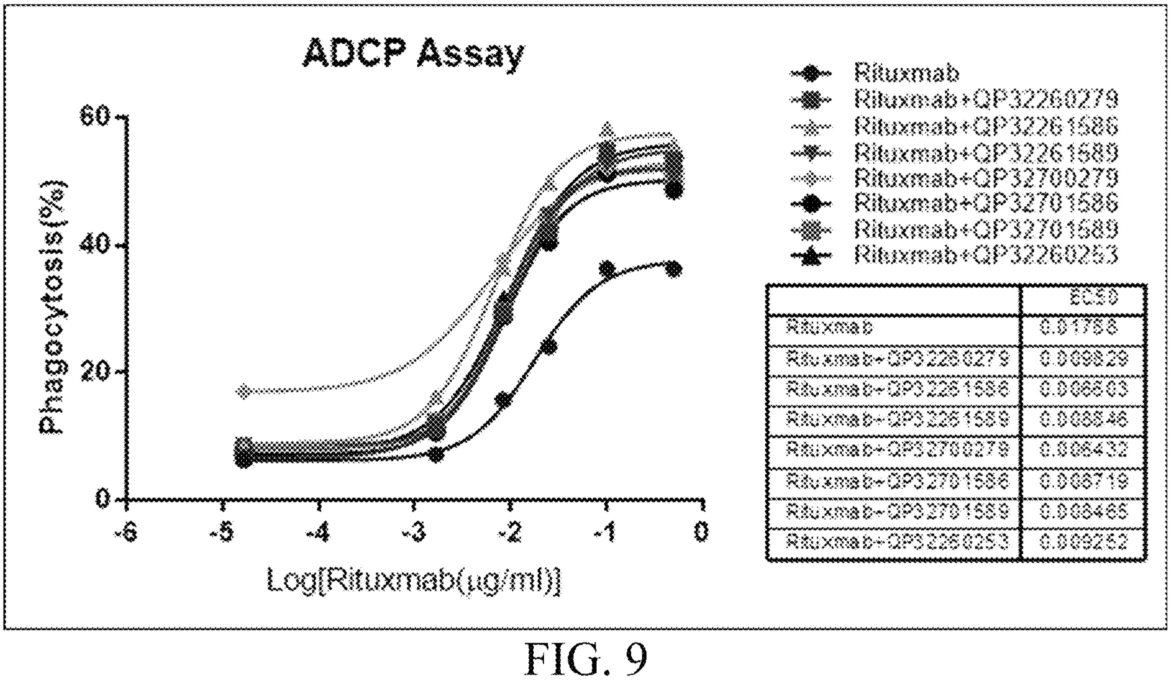
FIG. 9 to FIG. 11 show the ADCP results of in vitro functional assay for anti-SIRPα antibodies.
Figure 10:
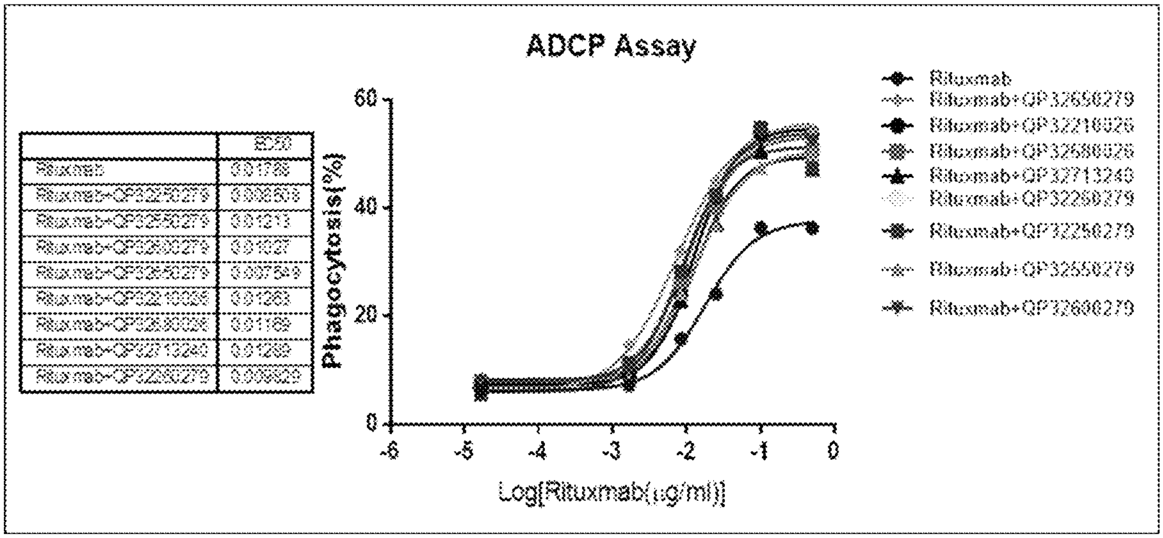
Figure 11:
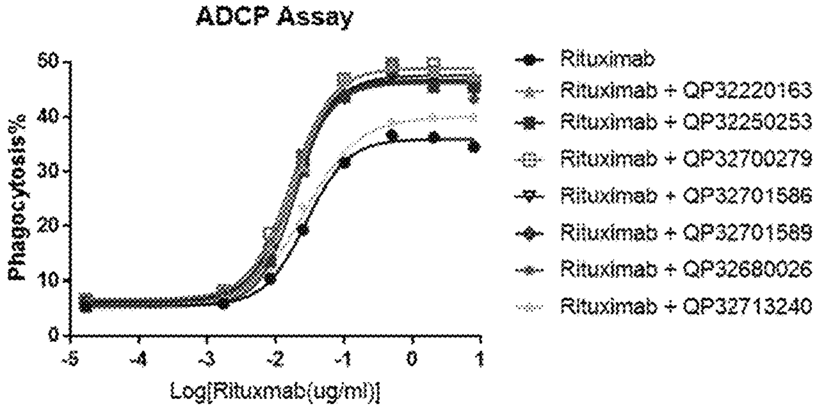

The affinity mature molecule and the control antibody were used for ADCP assay in cooperation with Rituximab, and the experimental results show that the combination of anti-SIRPα antibody and Rituximab has a smaller EC50 and a significantly greater synergistic effect of ADCP than Rituximab alone. The results are shown in FIGS. 9, 10 and 11.

Example 7: Evaluation of the Inhibition of Raji-Luc Tumor Growth by Anti-SIRPα Antibody QP32700279 in the B-NDG-hSIRPA Mouse Model In order to investigate the tumor killing effect of anti-SIRPα antibody, the Raji-Luc tumor model was inoculated intravenously with B-NDG-hSIRPα to evaluate the inhibitory effect of SIRPα antibodies and Rituximab on tumor growth. Raji-Luc cells were cultured in RPMI1640 medium containing 10% fetal bovine serum. PBS-resuspended Raji-Luc cells were inoculated into the tail vein of the B-NDG-hSIPRa mouse at a concentration of $5\times10^5$ cells/0.2 mL in a volume of 0.2 mL/mouse. On day 0 and day 3 after inoculation, the tumor imaging signal value was measured with a small animal imager. When the average imaging signal intensity reached about $1\times10^6$ P/S, appropriate animals were selected according to the tumor imaging signal value and animal weight into the group, and were evenly distributed to 4 experimental groups, with 8 animals in each experimental group. The administration was started on the day of grouping, and the specific administration scheme is shown in the following table:

| Group | Sample | Animal Numbers (mouse) | Dosage (mg/kg)[a] | Administration route | Administration Frequency[b] | Administration Times |
|---|---|---|---|---|---|---|
| G1 | Solvent control PBS | 8 | — | i.p. | Q3D | 6 |
| G2 | Rituximab | 8 | 0.1 | i.v. | Q2W | 2 |
| G3 | QP32700279 | 8 | 10 | i.p. | Q3D | 6 |
| G4 | QP32700279 + Rituximab | 8 | 10 + 0.1 | i.p. + i.v. | Q3D + Q2W | 6 + 2 |

Note:
[a]The administration volume is calculated as 10 μL/g according to the body weight of the experimental animal.
[b]Q3D refers to administration once every 3 days, and Q2W refers to administration once every 2 weeks.

Figure 12:
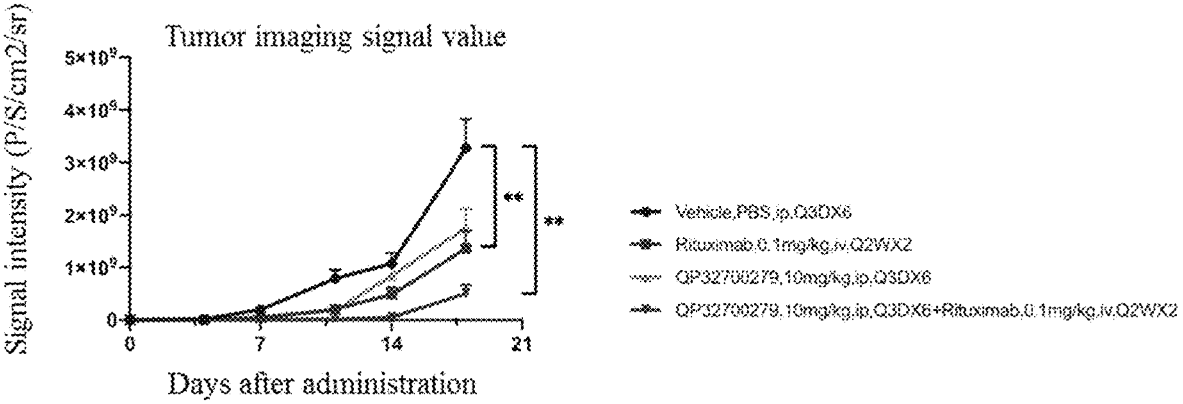
FIG. 12 shows the tumor growth curve reflected by the tumor imaging signal value in each group and the D18 imaging signal intensity result.

The day of grouping and administrating is defined as D0, up to D18, the tumor growth curve reflected by tumor imaging signal values of each group and imaging signal intensity data on D18 are shown in FIG. 12 and the table below:

| Group | D18 Signal intensity P/S/cm$^2$/sr | D18 TGI % | p value v.s. G1 |
|---|---|---|---|
| G1 | 3.28E9 ± 5.46E8/D18 | — | — |
| G2 | 1.36E9 ± 3.49E8/18 | 58.6% | 0.0027** |
| G3 | 1.76E9 ± 3.72E8/D18 | 46.4% | 0.0167* |
| G4 | 5.08E8 ± 1.6E8/D18 | 84.5% | <0.0001** |

The results of tumor growth curve show that the groups of Rituximab, QP32700279 and the combination of QP32700279 and Rituximab all significantly inhibit the growth of Raji-Luc tumors, and the tumor growth inhibition rate (TGI) is 58.6%, 46.4% and 84.5%, respectively, and the combination group shows stronger anti-tumor activity than the single-drug groups.

Figure 13:
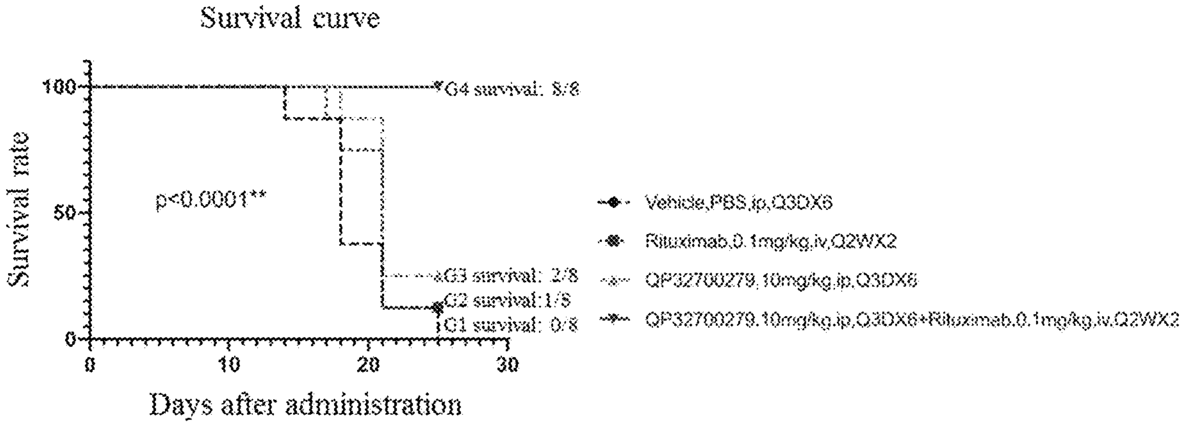
FIG. 13 shows the survival curves of each group.
Figure 14:
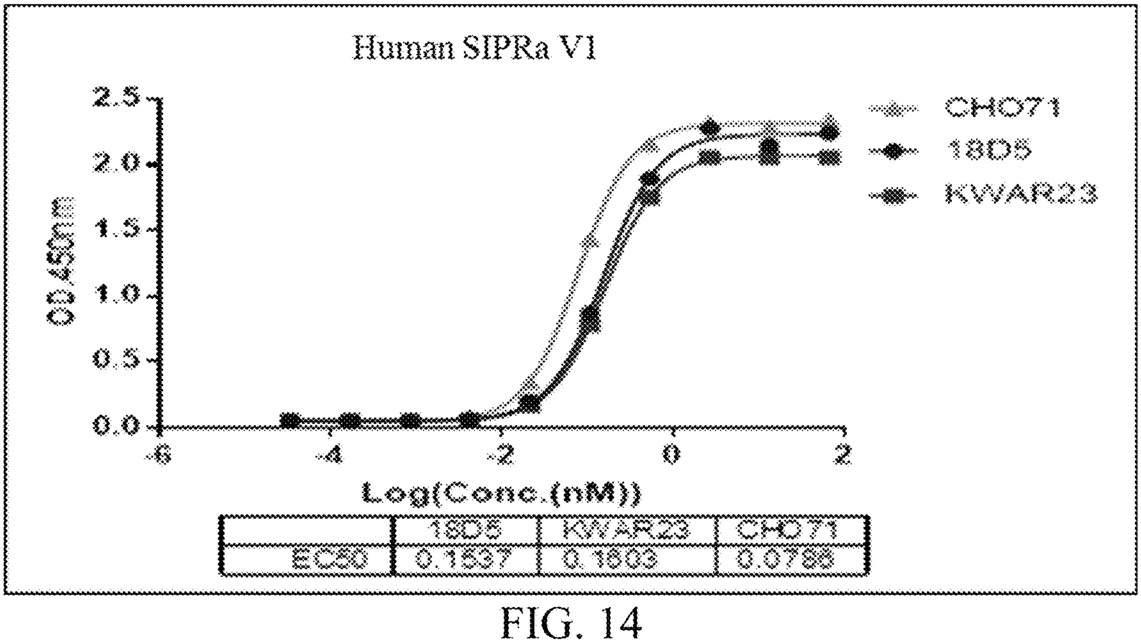
FIG. 14 to FIG. 23 show the results of ELISA detection of the binding of the antibody CHO71 of the present invention and the control antibodies 18D5 and KWAR23 to SIRPα V1/V2/V3/V4/V5/V6/V7/V8/V9/V10 subtypes.
Figure 15:
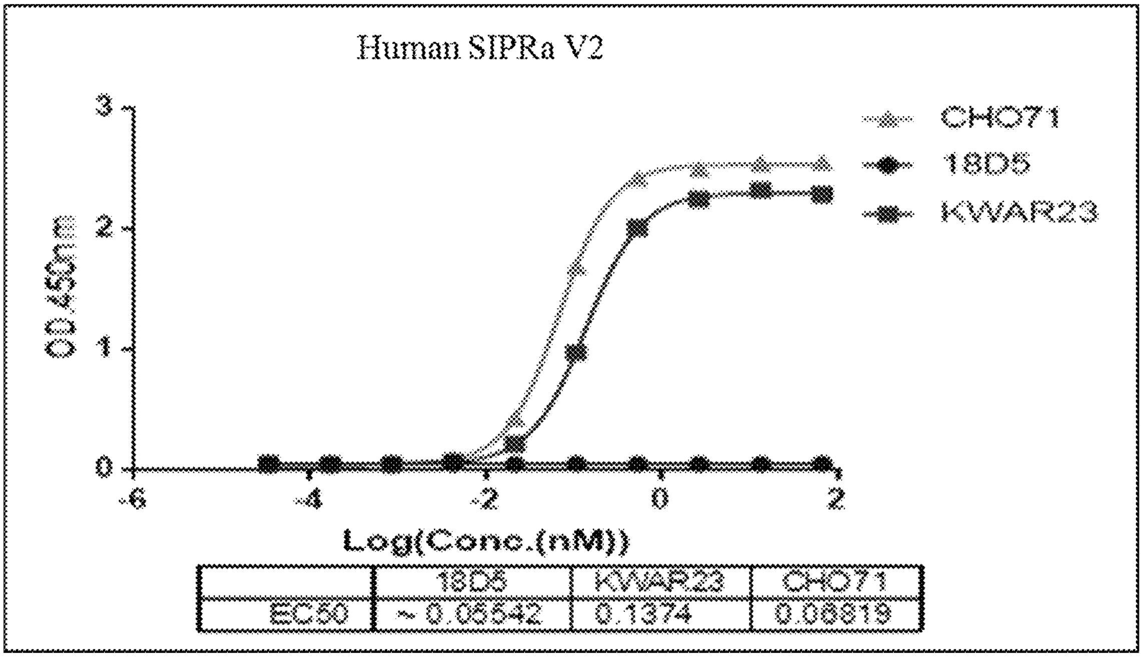
Figure 16:
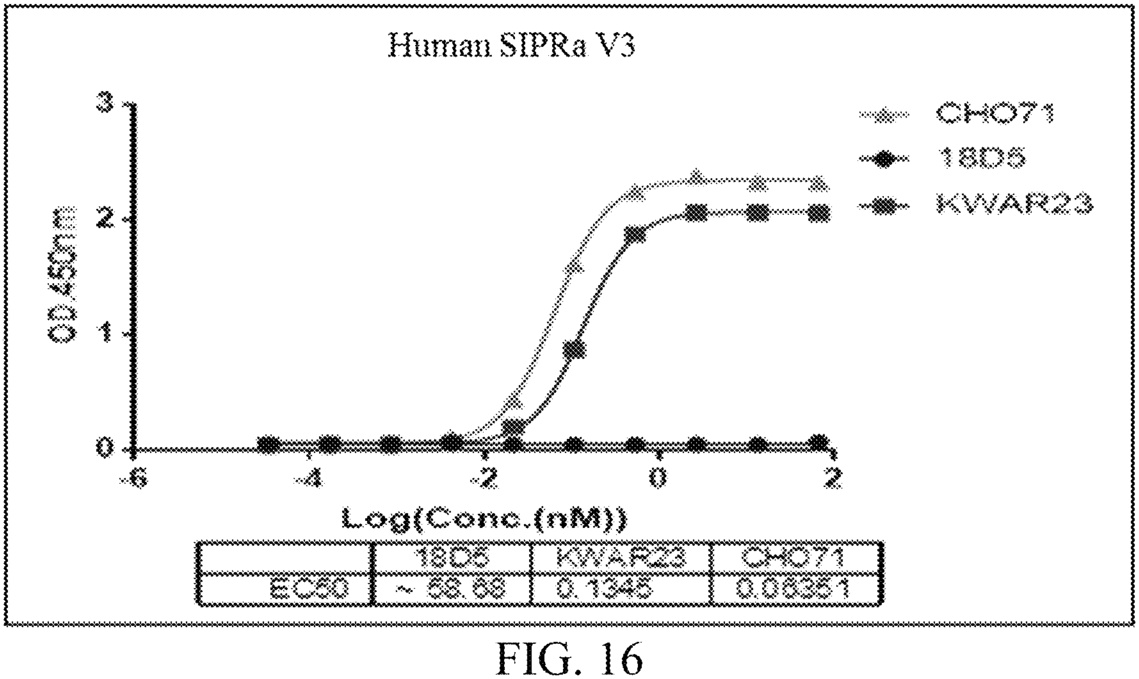
Figure 17:
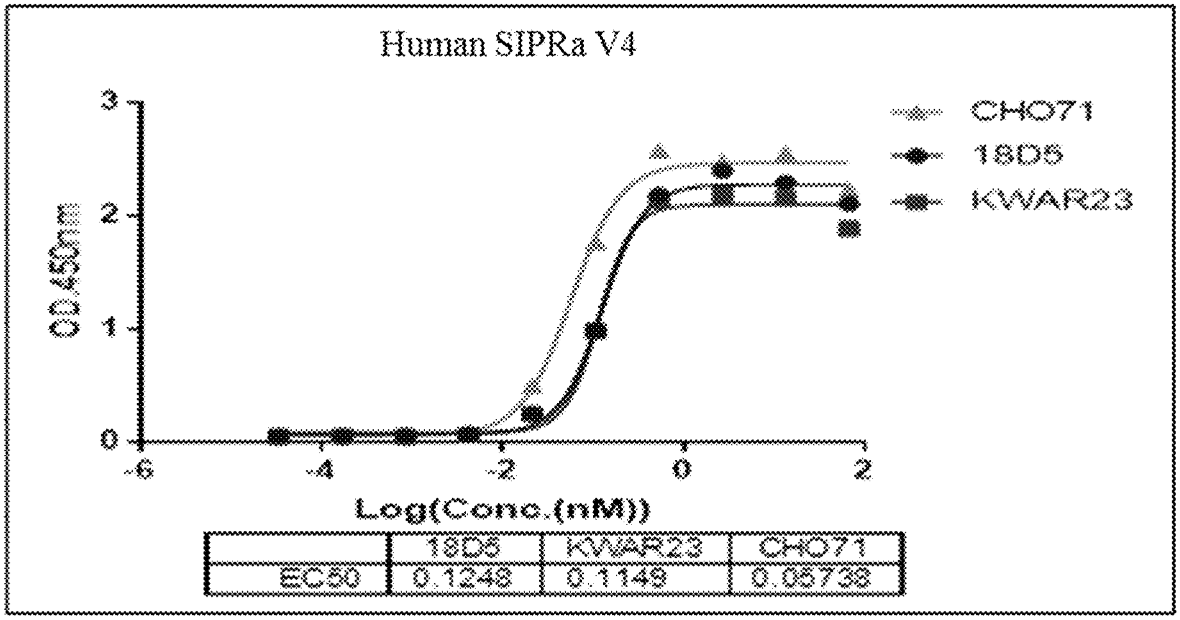
Figure 18:
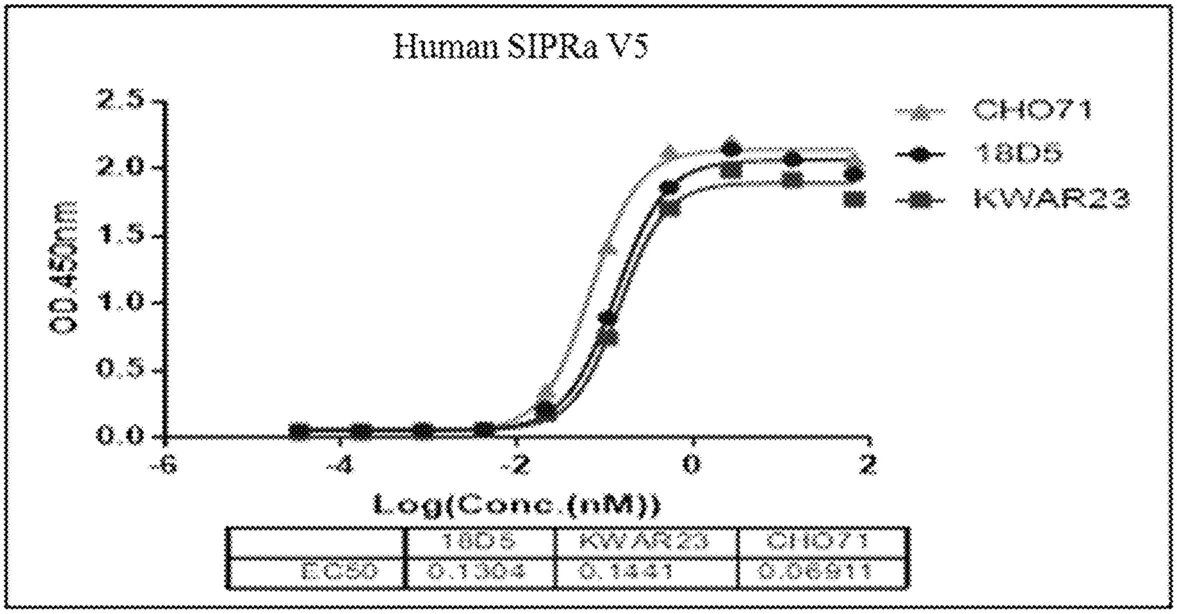
Figure 19:
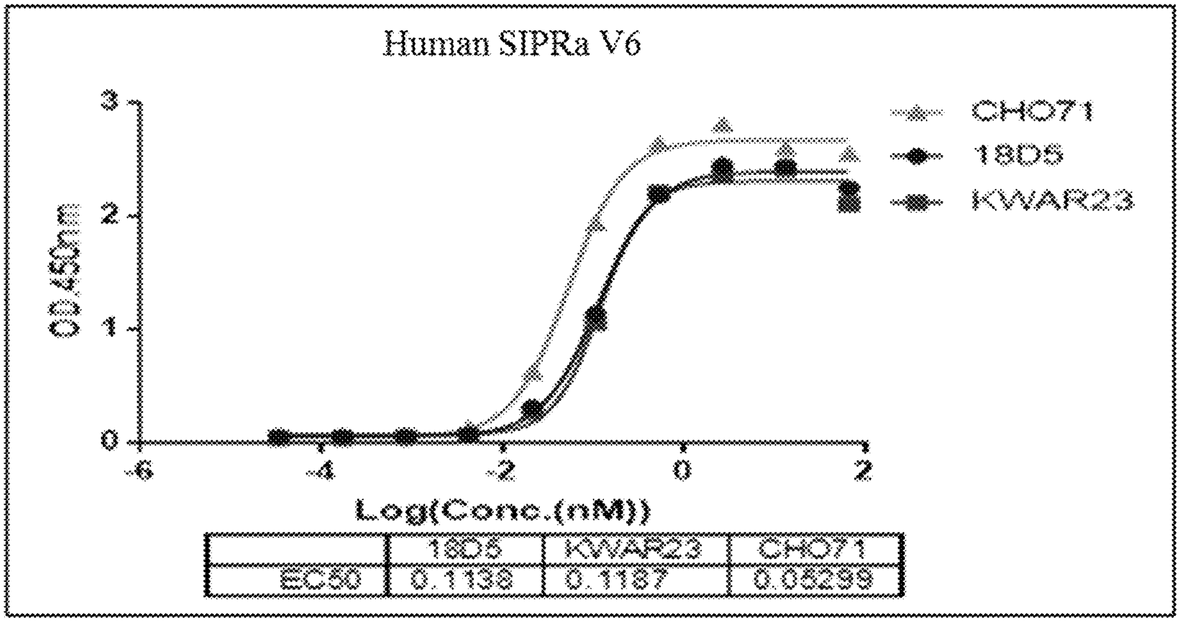
Figure 20:
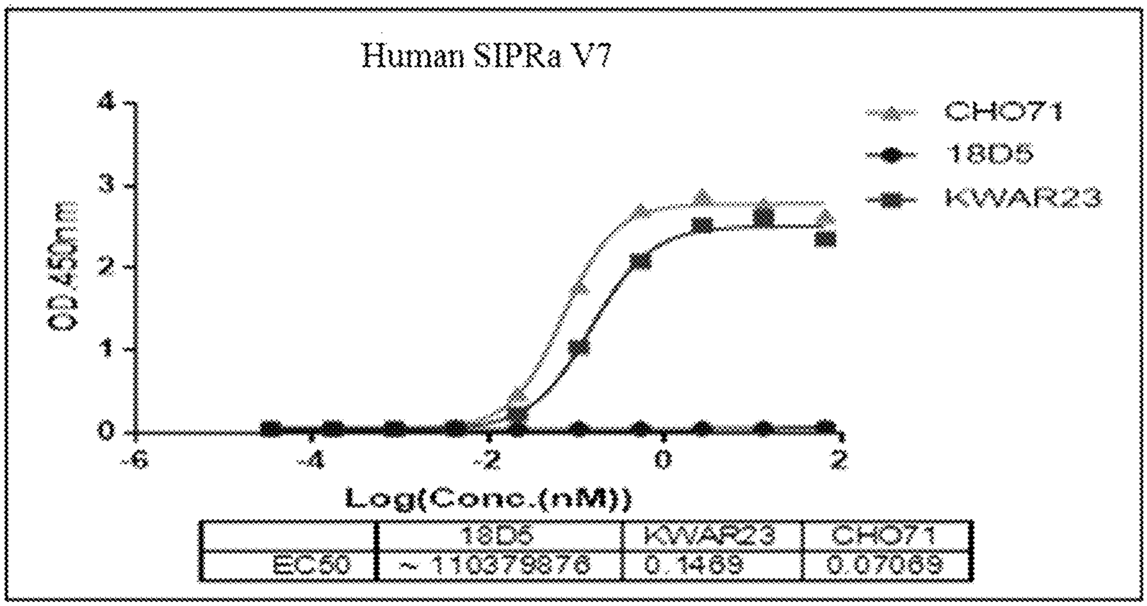
Figure 21:
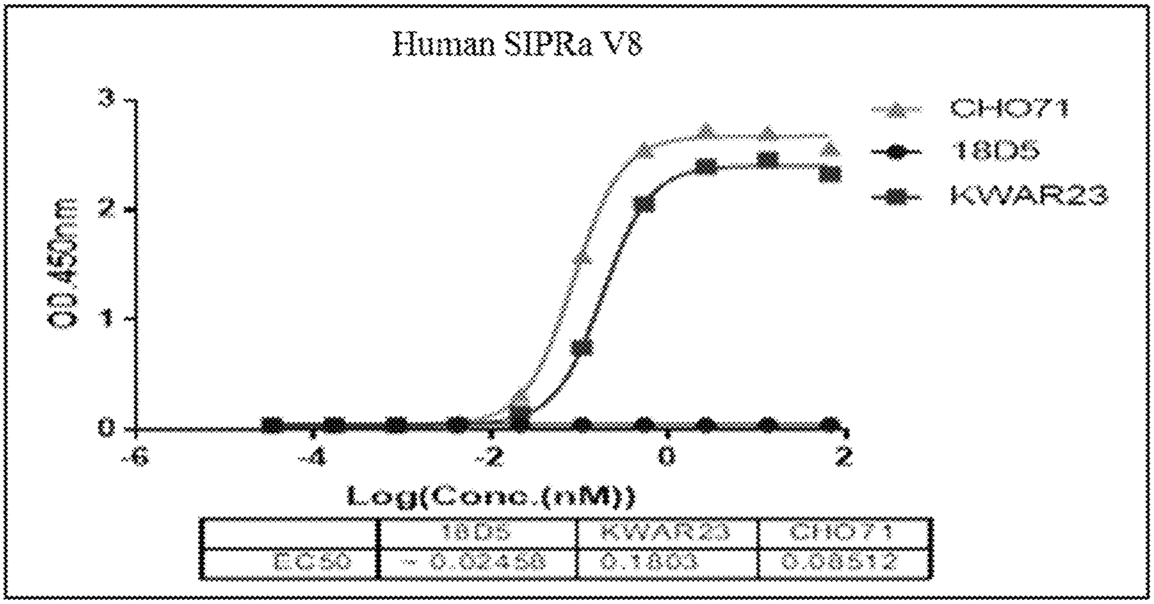
Figure 22:
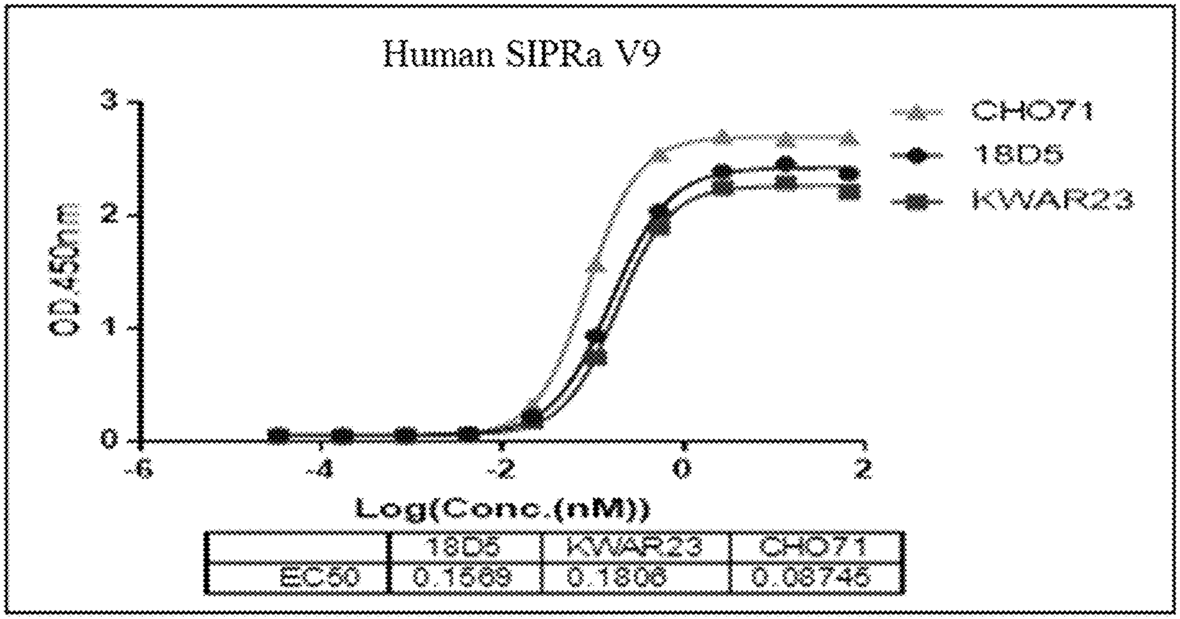
Figure 23:
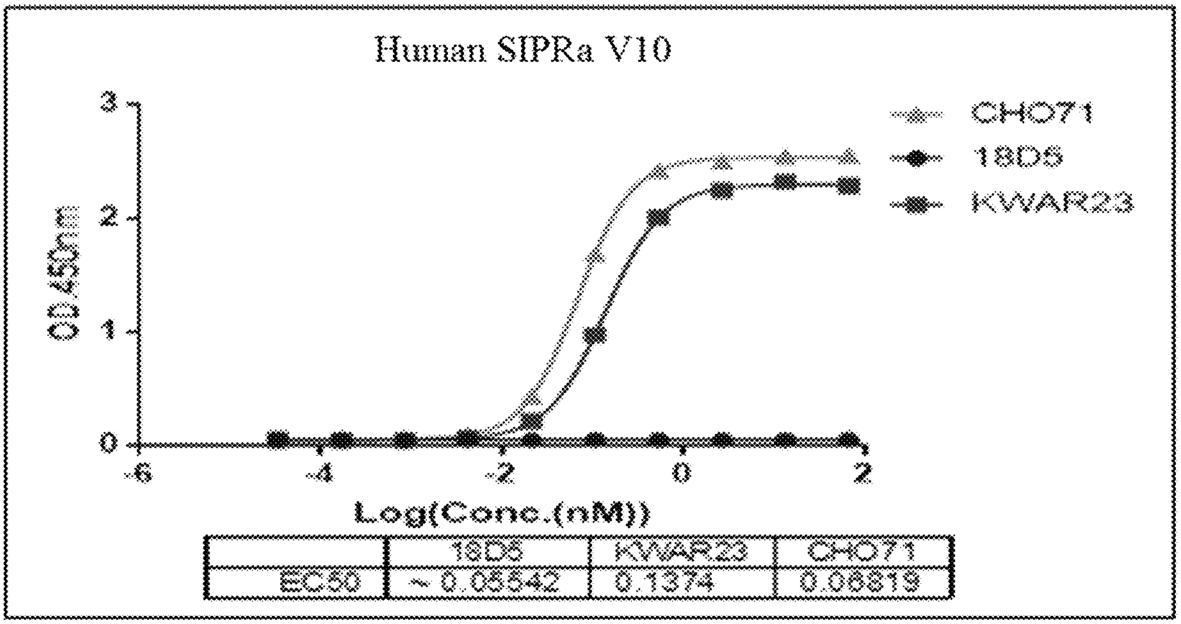

Due to the characteristics of the model, the mice would have abnormal action or paralysis in the later stage of the experiment. At this time, the mice would be euthanized and the survival curve would be recorded. By the end of all mice in G1 group died (D25), the survival curve of each group is shown in FIG. 13.

Kaplan-Meier method was used for survival analysis, Log rank test was used for inter-group comparison, $p<0.05$ is regarded as significant difference. Compared with the control group, both the QP32700279 group and the combined administration group (QP32700279+Rituximab) could significantly prolong the survival of Raji-Luc tumor-bearing mice (p=0.0445*, p<0.001**), while the Rituximab group could not effectively prolong the survival of tumor-bearing mice (p=0.23). The results suggest that QP32700279 and the combination of QP32700279 and Rituximab can effectively inhibit the tumor growth of Raji-Luc tumor-bearing mice and improve the survival of mice.

Example 8: ELISA Detection of Anti-SIRPα Antibody Binding to all Subtypes of Human SIRPα

According to the SIRPα V1/V2/V4/V5/V6/V7/V8/V9/V10 sequences reported by the prior literature ("Velcro" Engineering of High Affinity CD47 Ectodomain as Signal Regulatory Protein(SIRP alpha) Antagonists That Enhance Antibody-dependent Cellular Phagocytosis, JOURNAL OF BIOLOGICAL CHEMISTRY, VOLUME 290 NUMBER 20 May 15, 2015), the Fc (mouse IgG2a) of mouse IgG2a subtype was fused to the C-terminal of SIRPα above through gene synthesis and constructed into eukaryotic expression vector pQD. The supernatant of 293E transient transfection at the fifth day was purified by Protein A to obtain SIRPα V1/V2/V3/V4/V5/V6/V7/V8/V9/V10 fusion Fc (mouse IgG2a) proteins respectively. ELISA was further performed to detect binding of SIRPα antibodies to all subtypes of SIRPα. The sequences are shown below.

```
>SIRPα V1
                                        (SEQ ID NO: 51)
GVAGEEELQVIQPDKSVLVAAGETATLRCTATSLIPVGPIQWFRGAGPG
RELIYNQKEGHFPRVTTVSDLTKRNNMDFSIRIGNITPADAGTYYCVKF
RKGSPDDVEFKSGAGTELSVRAKPS

>SIRPα V2
                                        (SEQ ID NO: 52)
GVAGEEELQVIQPDKSVSVAAGESAILHCTVTSLIPVGPIQWFRGAGPA
RELIYNQKEGHFPRVTTVSESTKRENMDFSISISNITPADAGTYYCVKF
RKGSPDTEFKSGAGTELSVRAKPS

>SIRPα V3
                                        (SEQ ID NO: 53)
GVAGEEELQVIQPDKSVSVAAGESAILLCTVTSLIPVGPIQWFRGAGPA
RELIYNQKEGHFPRVTTVSESTKRENMDFSISISNITPADAGTYYCVKF
RKGSPD-TEFKSGAGTELSVRAKPS

>SIRPα V4
                                        (SEQ ID NO: 54)
GVAGEEGLQVIQPDKSVSVAAGESAILHCTATSLIPVGPIQWFRGAGPG
RELIYNQKEGHFPRVTTVSDLTKRNNMDFSIRIGNITPADAGTYYCVKF
RKGSPDDVEFKSGAGTELSVRAKPS

>SIRPα V5
                                        (SEQ ID NO: 55)
GVAGEEELQVIQPDKFVLVAAGETATLRCTATSLIPVGPIQWFRGAGPG
RELIYNQKEGHFPRVTTVSDLTKRNNMDFSIRIGNITPADAGTYYCVKF
RKGSPDDVEFKSGAGTELSVRAKPS

>SIRPα V6
                                        (SEQ ID NO: 56)
GVAGEEELQVIQPDKSVLVAAGETATLRCTATSLIPVGPIQWFRGAGPG
```

-continued

RELIYNQKEGHFPRVTTVSDLTKRNNMDFPIRIGNITPADAGTYYCVKF
RKGSPDDVEFKSGAGTELSVRAKPS

>SIRPα V7
(SEQ ID NO: 57)
GVAGEEELQVIQPDKSVSVAAGESAILHCTVTSLIPVGPIQWFRGAGPA
RELIYNQKEGHFPRVTTVSESTKRENMDFSISISNITPADAGTYYCVKF
RKGSPD-TEFKSGAGTELSVRGKPS

>SIRPα V8
(SEQ ID NO: 58)
GVAGEEELQVIQPDKSVLVAAGETATLRCTATSLIPVGPIQWFRGAGPA
RELIYNQKEGHFPRVTTVSESTKRENMDFSISISNITPADAGTYYCVKF
RKGSPD-TEFKSGAGTELSVRAKPS

>SIRPα V9
(SEQ ID NO: 59)
GVAGEEELQVIQPDKSVLVAAGETATLRCTATSLIPVGPIQWFRGAGPG
RELIYNQKEGHFPRVTTVSDLTKRNNMDFSIRISNITPADAGTYYCVKF
RKGSPDDVEFKSGAGTELSVRAKPS

>SIRPα V10
(SEQ ID NO: 60)
RVAGEEELQVIQPDKSVSVAAGESAILHCTVTSLIPVGPIQWFRGAGPA
RELIYNQKEGHFPRVTTVSESTKRENMDFSISISNITPADAGTYYCVKF
RKGSPD-TEFKSGAGTELSVRAKPS

>FC (mouse IgG2a)
(SEQ ID NO: 61)
EPRGPTIKPCPPCKCPAPNLLGGPSVFIFPPKIKDVLMISLSPIVTCVV
VDVSEDDPDVQISWFVNNVEVHTAQTQTHREDYNSTLRVVSALPIQHQD
WMSGKEFKCKVNNKDLPAPIERTISKPKG
SVRAPQVYVLPPPEEEMTKKQVTLTCMVTDFMPEDIYVEWTNNGKTELN
YKNTEPVLDSDGSYFMYSKLRVEKKNWVERNSYSCSVVHEGLHNHHTTK
SFSRTPGK.

SIRPα antibody to be tested:

The SIRPα antibody QP256279 was stably expressed in CHOS cells, and the CHOS stable expression protein was numbered CHO71.

According to the sequence provided by WO2017178653, molecular cloning construction, expression and purification of anti-SIRPα antibody 18D5 of OSE Company were performed for experimental control. Meanwhile, as mentioned above, the QP026249 is the anti-SIRPα antibody KWAR23 of Forty Seven Company, which is expressed here as KWAR23.

Experimental steps of ELISA detection of SIRPα antibody binding to SIRPα V1/V2/V3/V4/V5/V6/V7/V8/V9/V10:

The plate was coated with SIRPα V1/V2/V3/V4/V5/V6/V7/V8/V9/V10 at 1 μg/ml, 60 μl/well overnight at 4 °C, and washed twice with PBST; blocked with 5% non-fat milk (Sangon) of 200 μl/well, incubated at room temperature for 1 h, and washed twice with PBST. Antibody was incubated at 10 μg/ml, diluted with 5 times for 10 gradients, 60 μl/well, incubated at room temperature for 1 h, and washed with PBST 5 times. Secondary antibody incubation: anti-hFab 1:10000, 60 μl/well, incubated at room temperature for 1 h, washed with PBST 5 times. Developing: TMB was equilibrated at room temperature for 1 h in advance, 100 μl/well, to develop for 10 min, 2M $H_2SO_4$ of 50 ul/well was used for termination, and reading was performed at 450 nm on microplate reader.

The experimental results are shown in FIGS. 14 to 23, the SIRPα antibody CHO71 of the present invention binds to all subtypes of SIRPα V1/V2/V3/V4/V5/V6/V7/V8/V9/V10. SIRPα antibody 18D5 from OSE does not bind to SIRPα V2/V3/V7/V8/V10.

Although the contents of the present invention has been described in detail with reference to the preferred embodiments above, it should be understood that the above description should not be considered as a limitation of the present invention. Various modifications and alternatives to the present invention will be obvious to those skilled in the art upon reading the foregoing. Therefore, the scope of protection of the present invention should be defined by the appended claims.

The invention claimed is:

1. An anti-SIRPα antibody or antigen-binding fragment thereof, which comprises: a heavy chain variable region and a light chain variable region; wherein, the heavy chain variable region comprises: VHCDR1, VHCDR2 and VHCDR3 with amino acid sequence as shown in SEQ ID NO: 3, 4 and 5, respectively; the light chain variable region comprises: VLCDR1, VLCDR2 and VLCDR3 with amino acid sequence as shown in any of the following groups;

(1) SEQ ID NO: 37, 38, and 9;
(2) SEQ ID NO: 39, 38, and 9;
(3) SEQ ID NO: 7, 40, and 9;
(4) SEQ ID NO: 7, 8, and 41;
(5) SEQ ID NO: 7, 8, and 42;
(6) SEQ ID NO: 7, 8, and 43;
(7) SEQ ID NO: 37, 38, and 41;
(8) SEQ ID NO: 44, 38, and 41;
(9) SEQ ID NO: 7, 8, and 9.

2. The anti-SIRPα antibody or the antigen-binding fragment thereof according to claim 1, wherein the variable region further comprises a FR region.

3. The anti-SIRPα antibody or antigen-binding fragment thereof according to claim 2, wherein the sequence of the FR region is murine-derived, the sequence of the heavy chain variable region is as shown in SEQ ID NO: 2, and the sequence of the light chain variable region is as shown in SEQ ID NO: 6;

or the FR region is human-derived, wherein the human-derived FR region comprises: a heavy chain FR region sequence and a light chain FR region sequence; the heavy chain FR region sequence is derived from a combined sequence of human germline heavy chains IGHV1-18 and IGHJ2*01, comprising FR1, FR2, and FR3 regions of human germline heavy chain IGHV1-18 and a FR4 region of human germline heavy chain IGHJ2*01; and the light chain FR region sequence is derived from a combined sequence of human germline light chains IGKV4-1 and IGKJ2*01, comprising FR1, FR2, FR3 regions of human germline light chain IGKV4-1 and a FR4 region of human germline light chain IGKJ2*01.

4. The anti-SIRPα antibody or antigen-binding fragment thereof according to claim 1, wherein the sequence of the heavy chain variable region is as shown in SEQ ID NO: 17; and the sequence of the light chain variable region is selected from any one of SEQ ID NO: 18, 19, 20, 21, 22, 23, 24, and 25.

5. The anti-SIRPα antibody or antigen-binding fragment thereof according to claim 1, wherein the anti-SIRPα antibody or antigen-binding fragment thereof further comprises: a heavy chain constant region selected from human IgG1, IgG2, IgG3, and IgG4 and a variant thereof; and a light chain constant region selected from human k, 2 chain and a variant thereof.

6. The anti-SIRPα antibody or antigen-binding fragment thereof according to claim 5, wherein the heavy chain constant region comprises: an Fc fragment or a variant thereof; and the variant of the Fc fragment is derived from IgG1, and comprises mutation sites according to EU Numbering: L234A, L235A, K338A.

7. The anti-SIRPα antibody or antigen-binding fragment thereof according to claim 1, wherein the heavy chain sequence of the anti-SIRPα antibody or antigen-binding fragment thereof is as shown in SEQ ID NO:26.

8. The anti-SIRPα antibody or antigen-binding fragment thereof according to claim 1, which is a monoclonal antibody, a bispecific antibody, or a multispecific antibody; or which is in a structural form of Fab, F(ab')2, Fv, or ScFv.

9. A pharmaceutical composition comprising the anti-SIRPα antibody or antigen-binding fragment thereof according to claim 1, and one or more pharmaceutically acceptable carriers, diluents or excipients.

10. A nucleic acid molecule encoding the anti-SIRPα antibody or antigen-binding fragment thereof according to claim 1.

11. A method for inhibiting or treating a disease, disorder or condition, which comprises a step of administration of the anti-SIRPα antibody or antigen-binding fragment thereof according to claim 1, wherein the disease, disorder or condition is cancer.

12. An antibody-drug conjugate comprising the anti-SIRPα antibody or antigen-binding fragment thereof according to claim 1.

13. A vector comprising the nucleic acid molecule according to claim 10.

14. A host cell obtained by transformation of the vector according to claim 13.

15. The method according to claim 11, wherein the administration is in combination with one or more other drugs.

16. The method according to claim 15, wherein the other drugs comprise Rituximab.

17. A method for detecting SIRPα in a sample, using the anti-SIRPα antibody or antigen-binding fragment thereof according to claim 1.

18. The method according to claim 11, wherein the cancer is solid tumor.

19. The method according to claim 11, wherein the cancer is selected from gastric cancer, lung cancer, pancreatic cancer, breast cancer, liver cancer, ovarian cancer, renal cancer, colorectal cancer, esophageal cancer, glioblastoma, melanoma, sarcoma.

* * * * *